United States Patent [19]

Longley et al.

[11] Patent Number: 5,840,750
[45] Date of Patent: Nov. 24, 1998

[54] DISCODERMOLIDE COMPOUNDS

[75] Inventors: Ross E. Longley; Sarath P. Gunasekera, both of Vero Beach; Shirley A. Pomponi, Fort Pierce, all of Fla.

[73] Assignee: Harbor Branch Oceanographic Institution, Inc., Fort Pierce, Fla.

[21] Appl. No.: 761,106

[22] Filed: Dec. 5, 1996

Related U.S. Application Data

[63] Continuation-in-part of Ser. No. 567,442, Dec. 5, 1995.

[51] Int. Cl.$^6$ .......................... A61K 31/35; C07D 309/30
[52] U.S. Cl. ............................................. 514/459; 549/292
[58] Field of Search .............................. 549/292; 514/459

[56] References Cited

U.S. PATENT DOCUMENTS

| | | | |
|---|---|---|---|
| 4,206,221 | 6/1980 | Miller et al. | 514/471 |
| 4,939,168 | 7/1990 | Gunasekera et al. | 514/559 |
| 4,960,790 | 10/1990 | Stella et al. | 514/449 |
| 5,157,049 | 10/1992 | Haugwitz et al. | 514/449 |

OTHER PUBLICATIONS

Nerenberg, J.B. et al. (1993) "Total Synthesis of the Immunosuppressive Agent (−)–Discodermolide" J. Am. Chem. Soc. 115:12621–12622.

Uemura, D. et al. (1985) "Norhalichondrin A: An Antitumor Polyether Macrolide from a Marine Sponge" J. Am. Chem. Soc. 107:4796–4798.

Faulkner, D.J. (1987) "Marine Natural Products" Natural Products Reports 4:539–576.

Fuchs, D.A., R.K. Johnson (1978) "Crtologic Evidence that Taxol, an Antineoplastic Agent from *Taxus brevifolia,* Acts as a Mitotic Spindle" Cancer Treatment Reports 62(8):1219–1222.

Schiff, P.B. et al. (1979) "Promotion of microtubule assembly in vitro by taxol" Nature (London) 22:665–667.

Rowinsky, E.K., R.C. Donehower (1995) "Paclitaxel (Taxol)" The New England Journal of Medicine 332(15):1004–1014.

Minale, L. et al. (1976) "Natural Products from Porifera" Fortschr. Chem. org. Naturst. 31:1–72.

Kelly–Borges et al. (1994) "Species Differentiation in the Marine Sponge Genus *Discodermia* (Demospongiae: Lithistida): the Utility of Ethanol Extract Profiles as Species–Specific Chemotaxonomic Markers" Biochemical Systematics and Ecology 22(4):353–365.

ter Haar, E., H.S. Rosenkranz, E. Hamel, B.W. Day (1996) "Computational and Molecular Modeling Evaluation of the Structural Basis for Tubulin Polymerization Inhibition by Colchicine Site Agents," *Bioorganic and Medicinal Chemistry* 4(10):1659–1671.

Hung, D.T., J. Chen. S.L. Schreiber (1996) "(+)–Discodermolide binds in microtubules in stoichiometric ratio to tubulin dimers, blocks binding and results in mitotic arrest," Chemistry & Biology 3(4):287–293.

*Primary Examiner*—Amelia Owens
*Attorney, Agent, or Firm*—Saliwanchik, Lloyd & Saliwanchik

[57] ABSTRACT

Novel lactone compounds from the marine sponge *Discodermia dissoluta* have been isolated. These compounds and their analogs have been shown to have activity against mammalian cancer cells, and can be used in treating human patients which host cancer cells, including leukemia, melanoma, and breast, colon, CNS, and lung tumors.

7 Claims, 21 Drawing Sheets

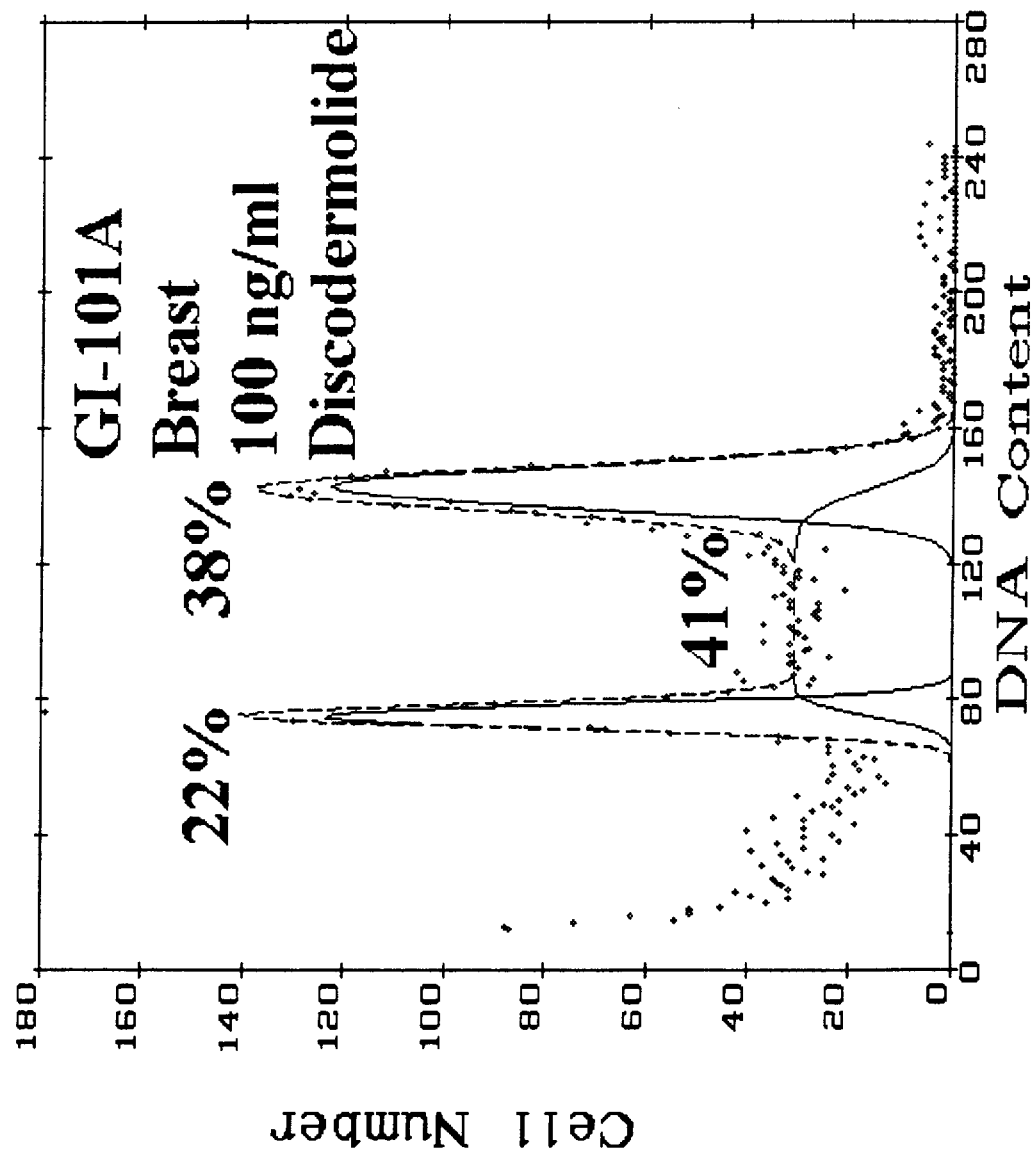

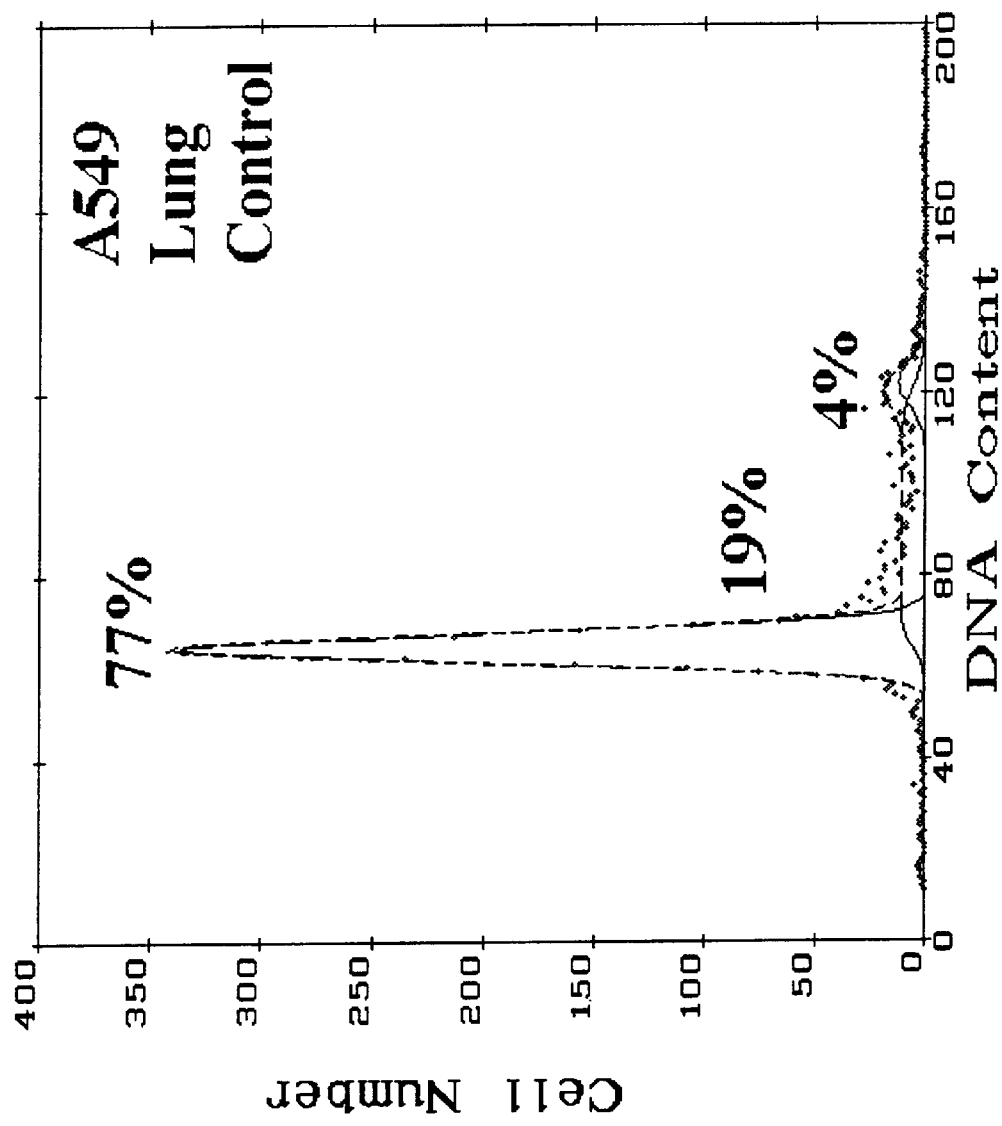

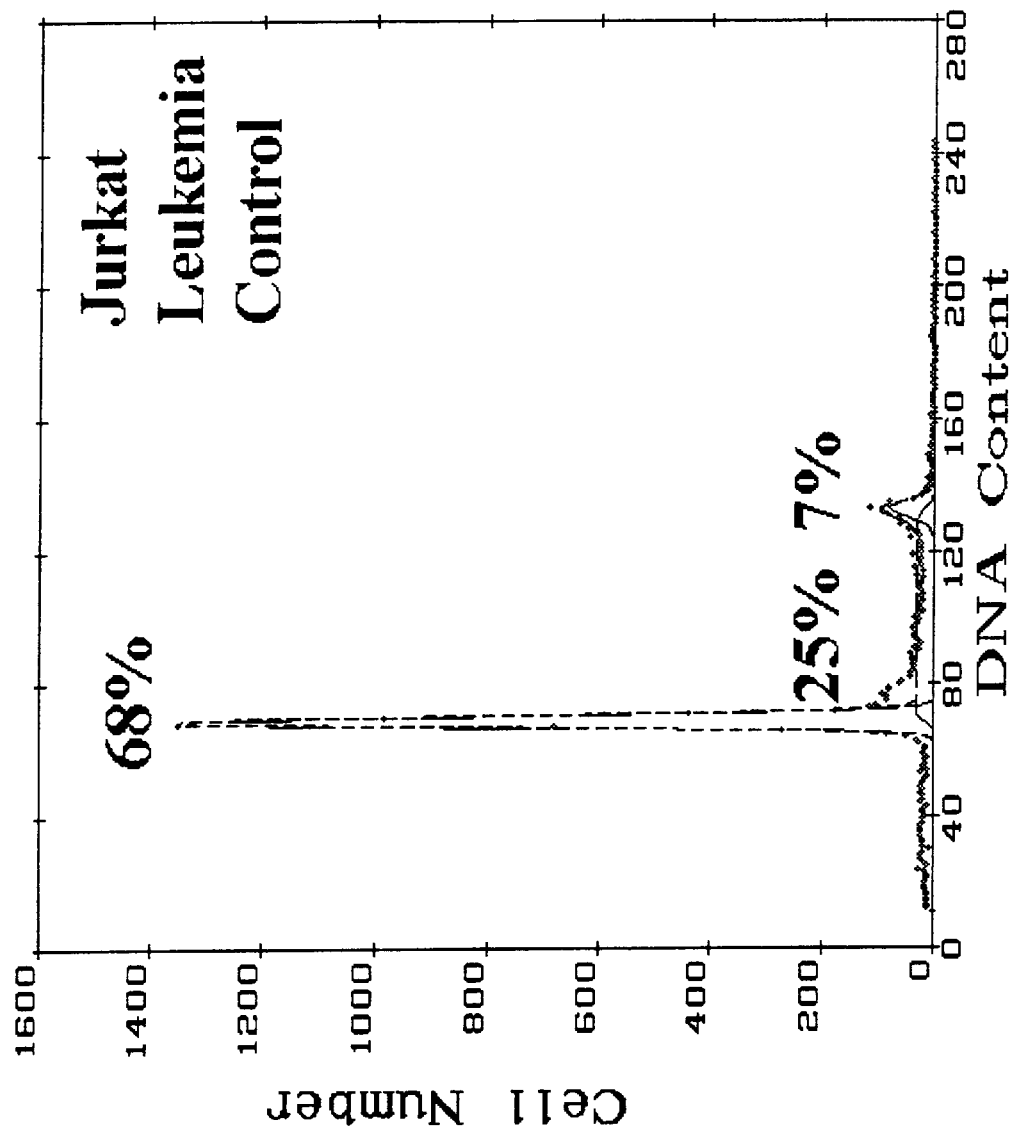

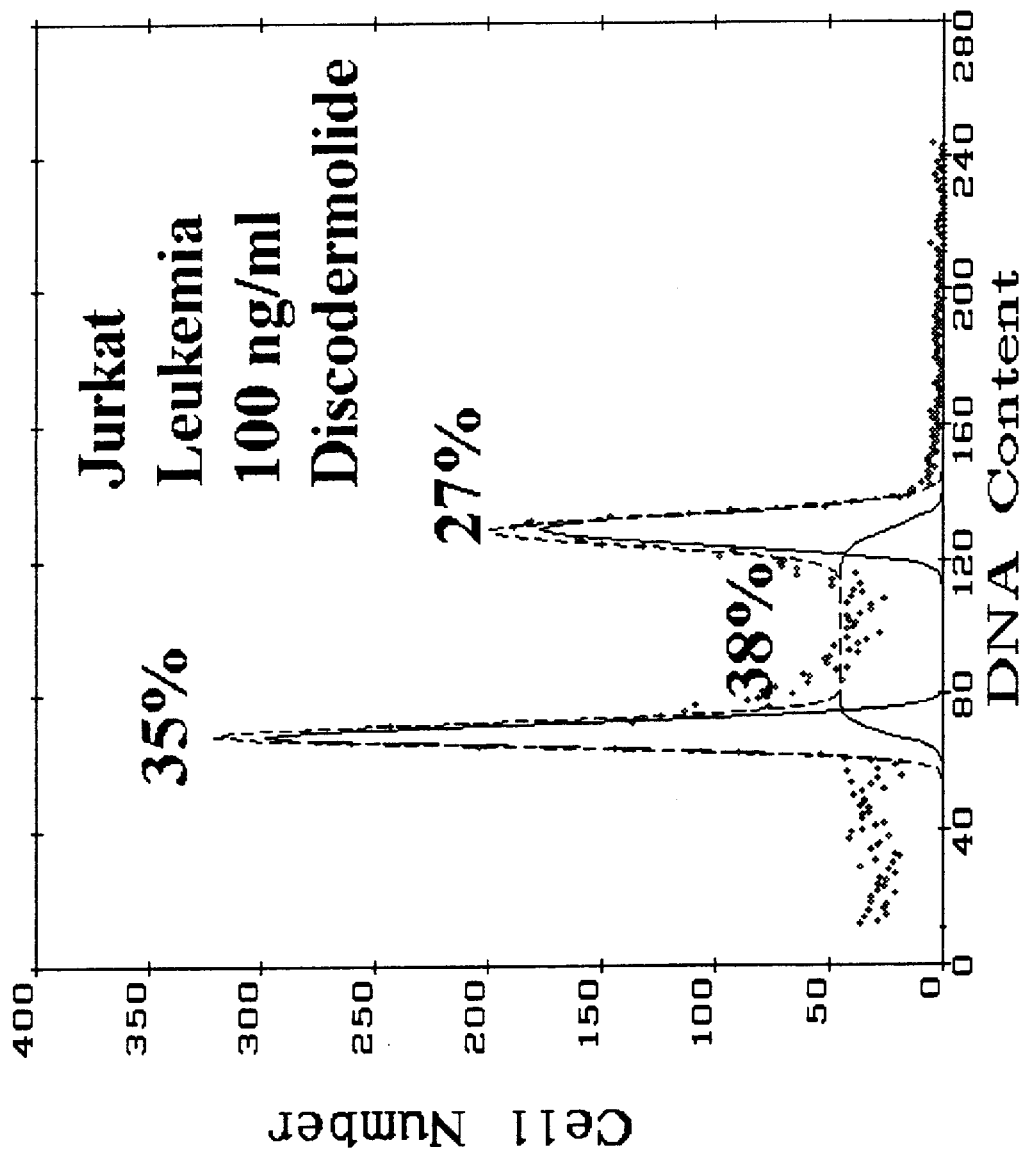

DISCODERMOLIDE COMPOUNDS

CROSS-REFERENCE TO A RELATED APPLICATION

This is a continuation-in-part of co-pending application Ser. No. 08/567,442, filed Dec. 5, 1995.

FIELD OF THE INVENTION

This invention relates to organic compounds and compositions which have useful therapeutic properties. More particularly, the invention concerns novel lactone compounds having immunomodulatory and antitumor activities, pharmaceutical compositions comprising such compounds, methods for the preparation of the novel compounds, and compositions and methods of their use for therapeutic purposes.

BACKGROUND OF THE INVENTION

In the past, considerable research and resources have been devoted to oncology and antitumor measures including chemotherapy. While certain methods and chemical compositions have been developed which aid in inhibiting, remitting, or controlling the growth of tumors, new methods and antitumor chemical compositions are needed.

In searching for new biologically active compounds, it has been found that some natural products and organisms are potential sources for chemical molecules having useful biological activity of great diversity. For example, the diterpene commonly known as taxol, isolated from several species of yew trees, is a mitotic spindle poison that stabilizes microtubules and inhibits their depolymerization to free tubulin (Fuchs, D. A., R. K Johnson [1978] *Cancer Treat. Rep.* 62:1219–1222; Schiff, P. B., J. Fant, S. B. Horwitz [1979] *Nature* (London) 22:665–667). Taxol is also known to have antitumor activity and has undergone a number of clinical trials which have shown it to be effective in the treatment of a wide range of cancers (Rowinski, E. K. R. C. Donehower [1995] *N. Engl. J. Med.* 332:1004–1014). See also, e.g., U.S. Pat. Nos. 5,157,049; 4,960,790; and 4,206,221.

Marine sponges have also proven to be a source of biologically active chemical molecules. A number of publications have been issued disclosing organic compounds derived from marine sponges including Scheuer, P. J. (ed.) *Marine Natural Products, Chemical and Biological Perspectives*, Academic Press, New York, 1978–1983, Vol. I–V; Uemura, D., K. Takahashi, T. Yamamoto, C. Katayama, J. Tanaka, Y. Okumura, Y. Hirata (1985) *J. Am. Chem. Soc.* 107:4796–4798; Minale, L. et al. (1976) *Fortschr. Chem. org. Naturst.* 33:1–72; Faulkner, D. J. (1996) *Natural Products Reports* 13:75–125, and references cited therein.

The present invention has added to the arsenal of antitumor compounds by the discovery of new classes of organic compounds possessing, inter alia, useful tubulin-polymerizing and antitumor activities. These compounds can be isolated from extracts of the marine sponge, *Discodermia dissoluta*. See U.S. Pat. Nos. 4,939,168 and 5,010,099. In addition, these compounds can be synthesized by known organic chemistry procedures that are readily understood by persons of ordinary skill in the art. Nerenberg, J. B. et al. (1993) *J. Amer. Chem. Soc.* 115:12621–12622.

BRIEF SUMMARY OF THE INVENTION

A principal object of this invention is the provision of novel compositions of biologically active, lactone compounds which can advantageously be used for treating cancer. More specifically, the novel compositions and methods of use can advantageously be useful in the treatment of a patient hosting cancer cells, for example, inhibiting the growth of tumor cells in a mammalian host. More particularly, the subject compounds, herein referred to as the discodermolides, and compositions comprising the discodermolides can be used for inhibiting in a human the growth of tumor cells, including cells of breast, colon, CNS, or lung tumors, as well as human leukemia or melanoma cells. It is understood that the mechanisms for achieving anticancer activity exhibited by the subject compounds would lead a person of ordinary skill in the art to recognize the applicability of the subject compounds, compositions, and methods to additional types of cancer as described herein.

In accordance with the invention, methods for inhibiting tumors in a host comprise contacting tumor cells with an effective amount of the new pharmaceutical compositions of the invention. The tumor cells inhibited by the invention are those which are susceptible to the subject compounds described herein or compositions comprising those compounds.

Additional objects of the invention are the provision of methods for producing the new compounds and compositions.

Other objects and further scope of applicability of the present invention will become apparent from the detailed descriptions given herein; it should be understood, however, that the detailed descriptions, while indicating preferred embodiments of the invention, are given by way of illustration only, since various changes and modifications within the spirit and scope of the invention will become apparent from such descriptions.

BRIEF DESCRIPTION OF THE DRAWINGS

FIGS. 2A–2C show the effect of discodermolides on GI-101A human breast cells according to the subject invention.

FIGS. 3A–3C show the effect of discodermolides on A549 human lung cells according to the subject invention.

FIGS. 4A–4C show the effect of discodermolides on Jurkat human leukemia cells.

DETAILED DISCLOSURE OF THE INVENTION

Figure 1A:
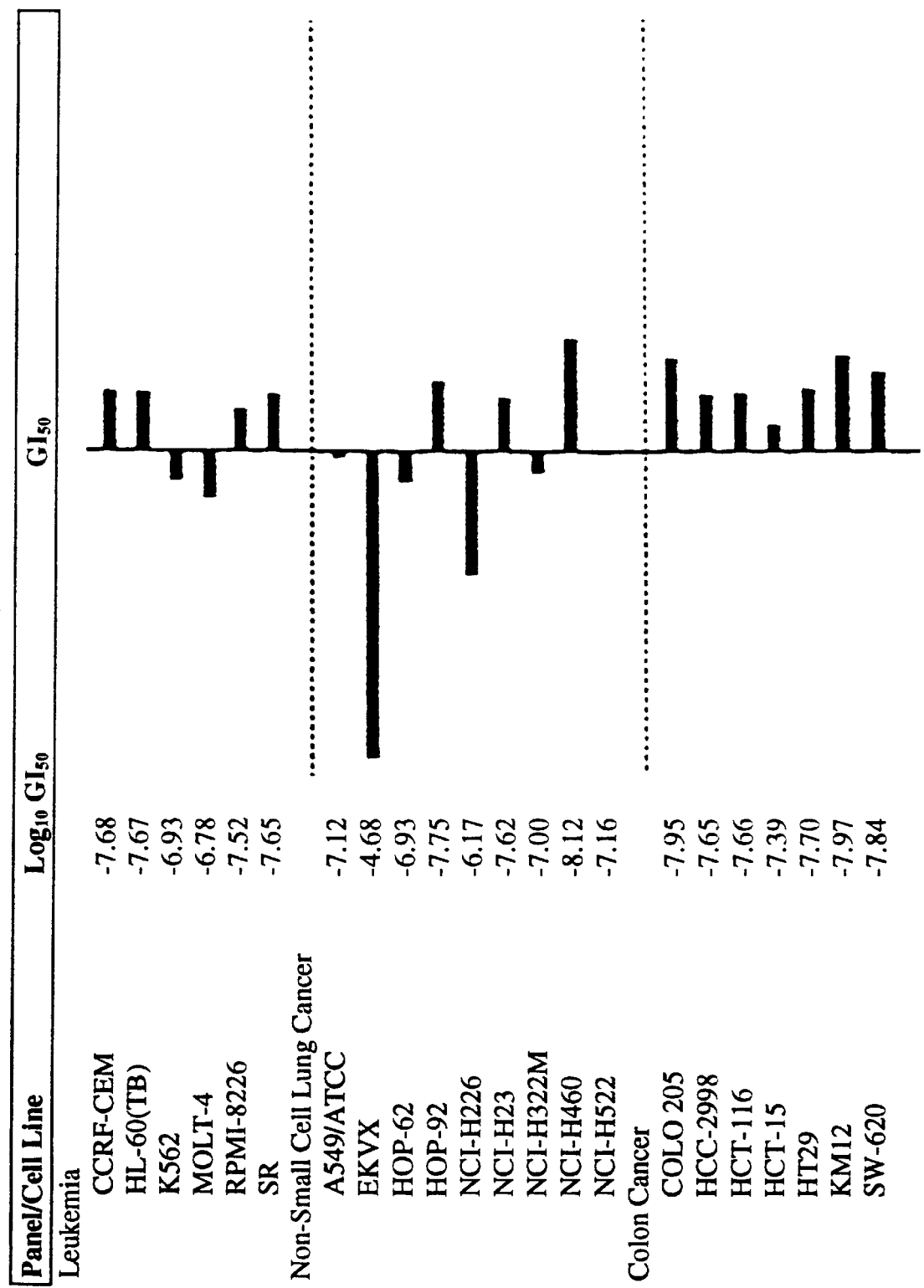
FIGS. 1A–1K show antiproliferative effects, measured by $GI_{50}$, TGI, and $LC_{50}$ of discodermolides against a plurality of human tumor cell lines.
Figure 1B:
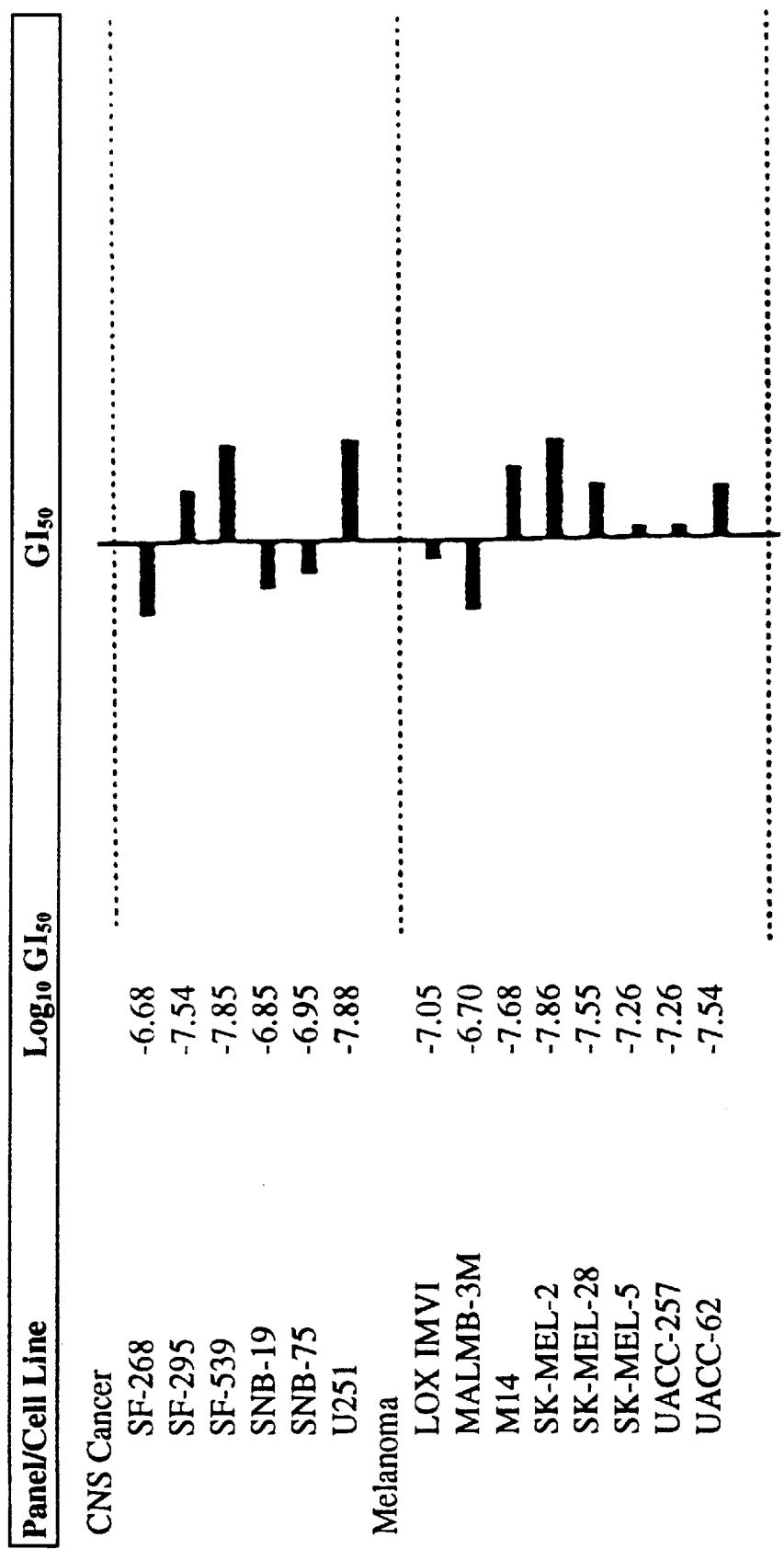
Figure 1C:
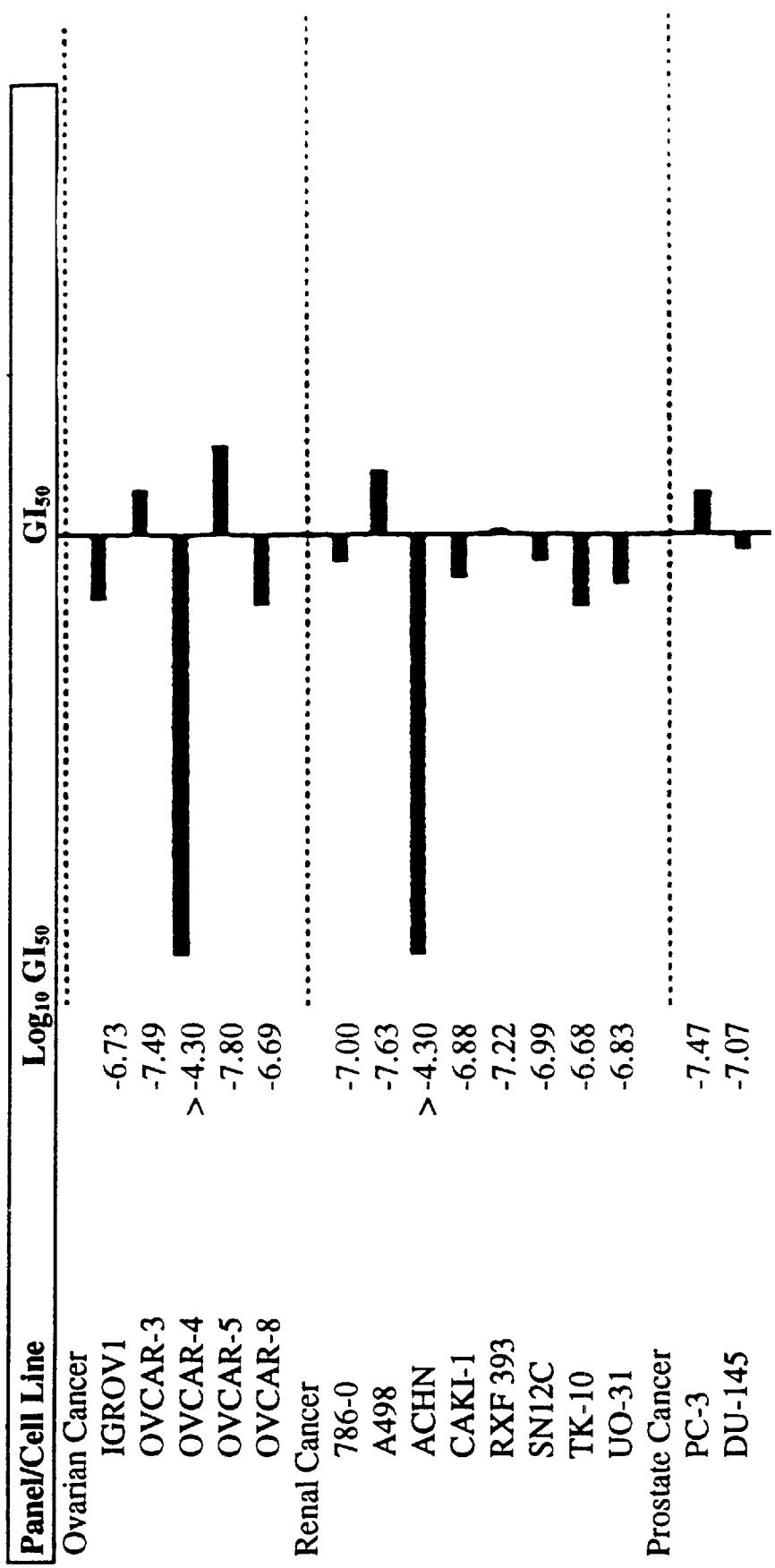
Figure 1D:
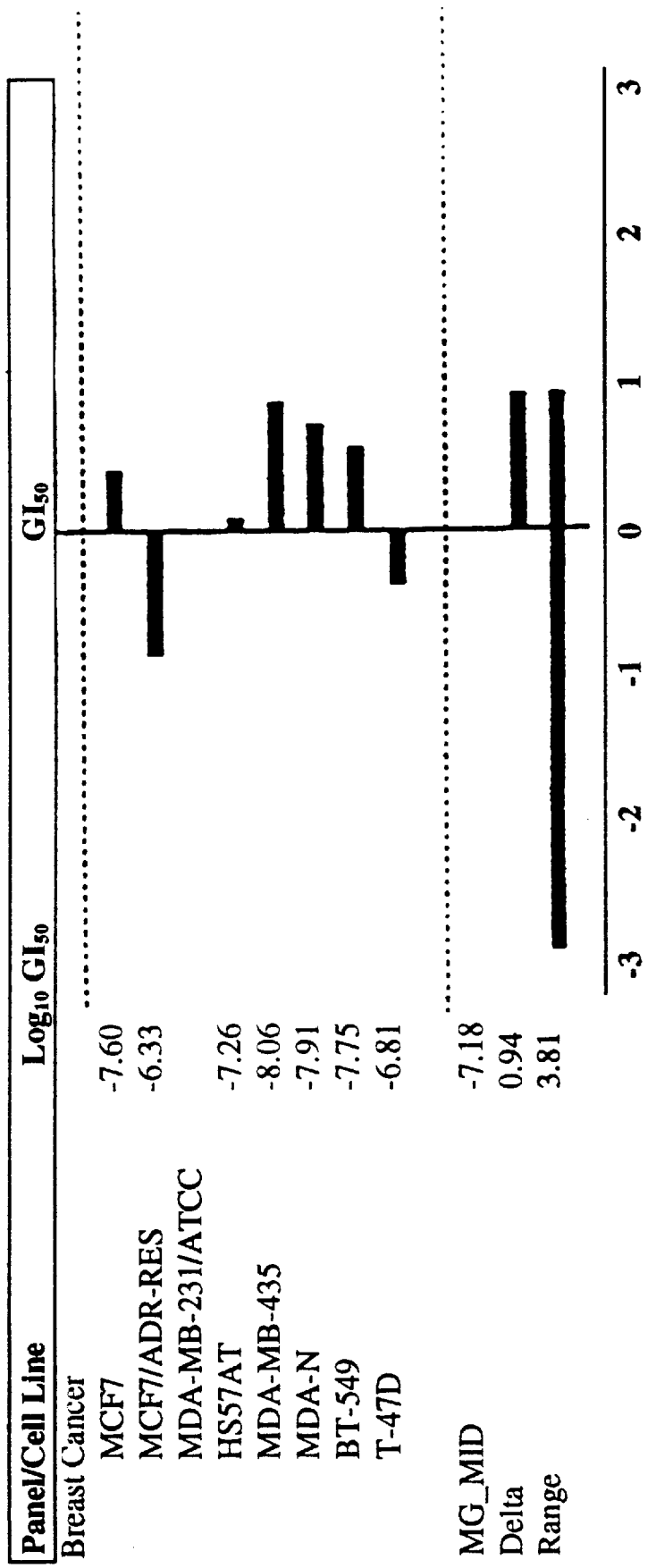
Figure 1E:
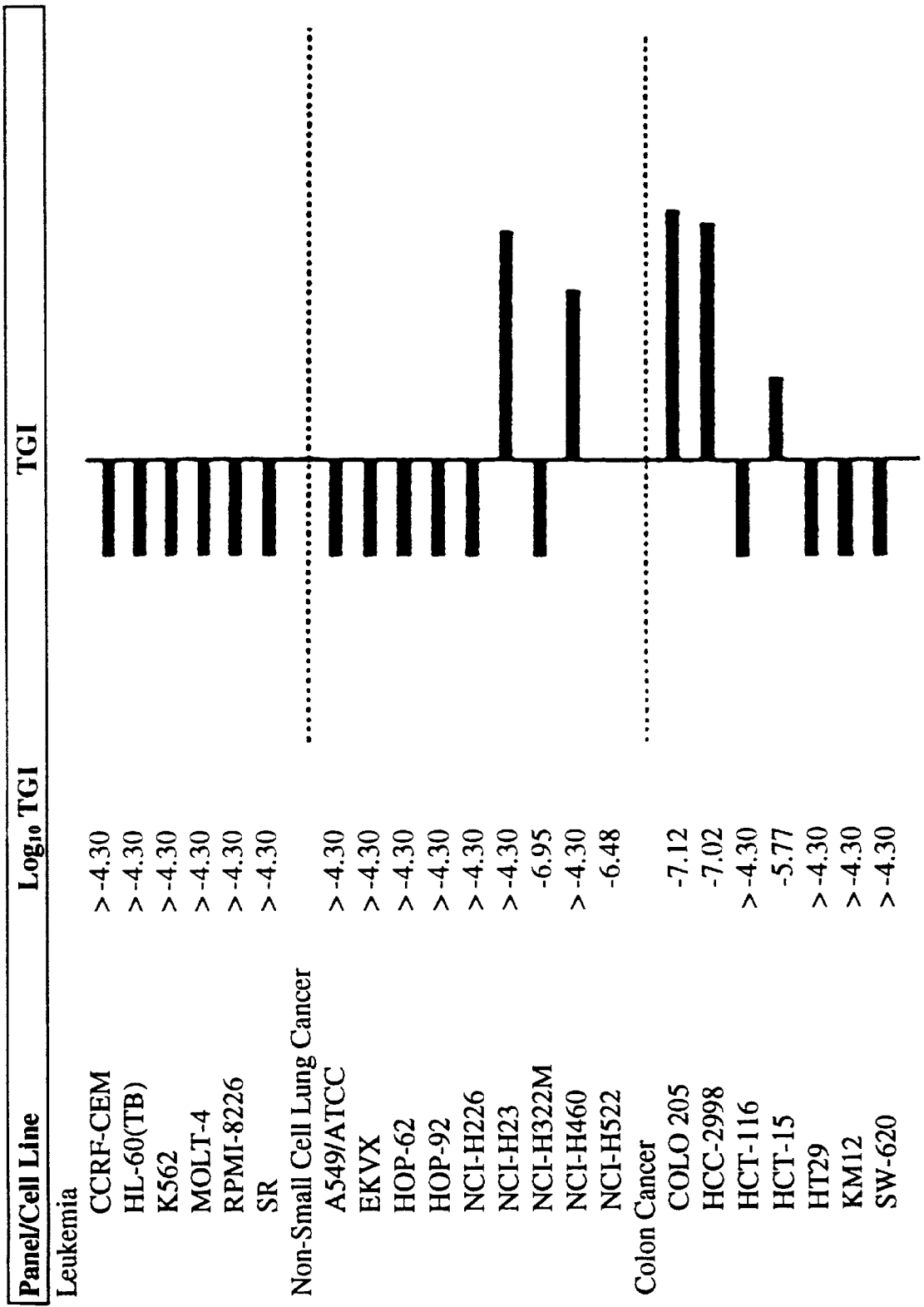
Figure 1F:
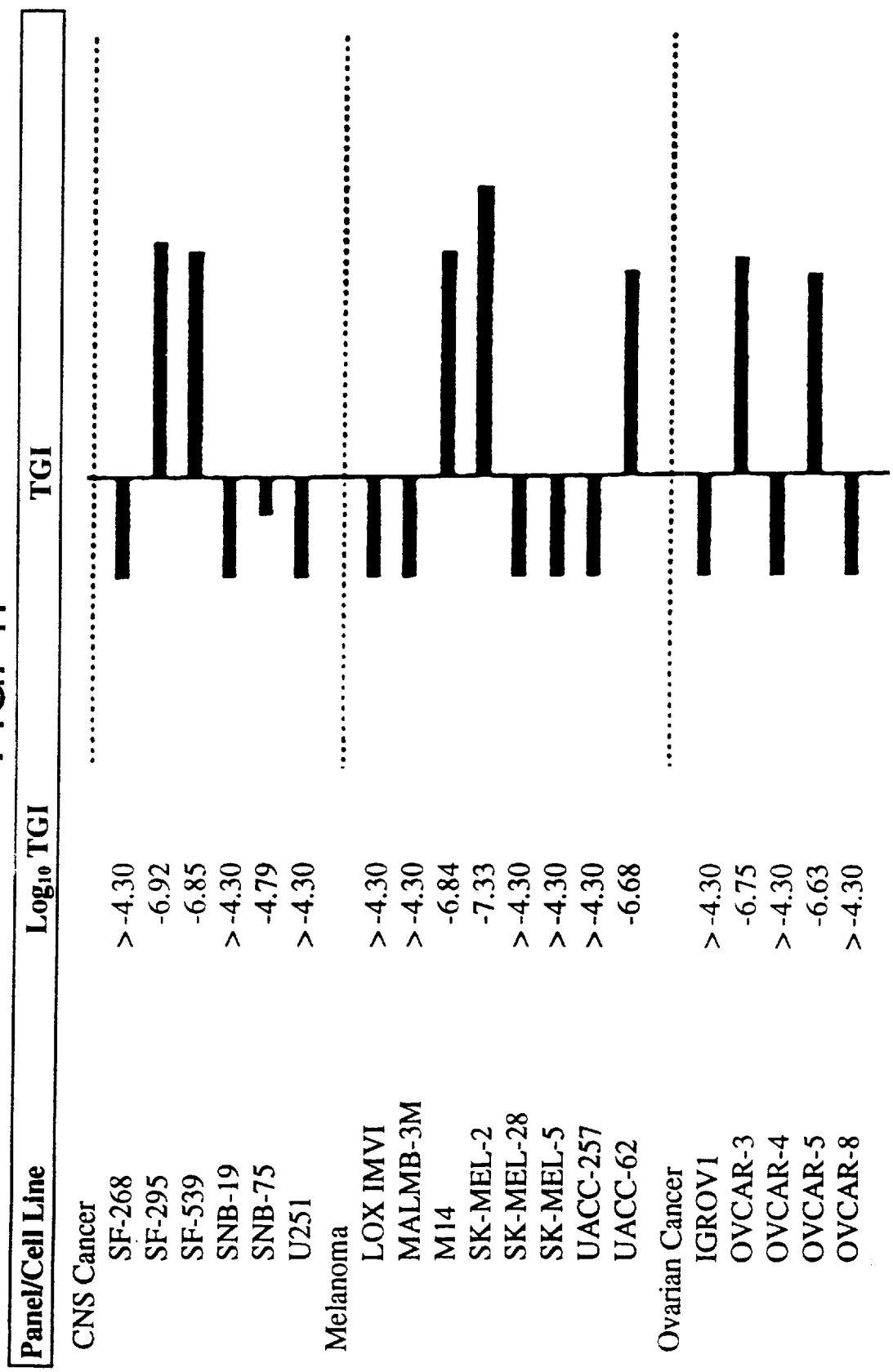
Figure 1G:
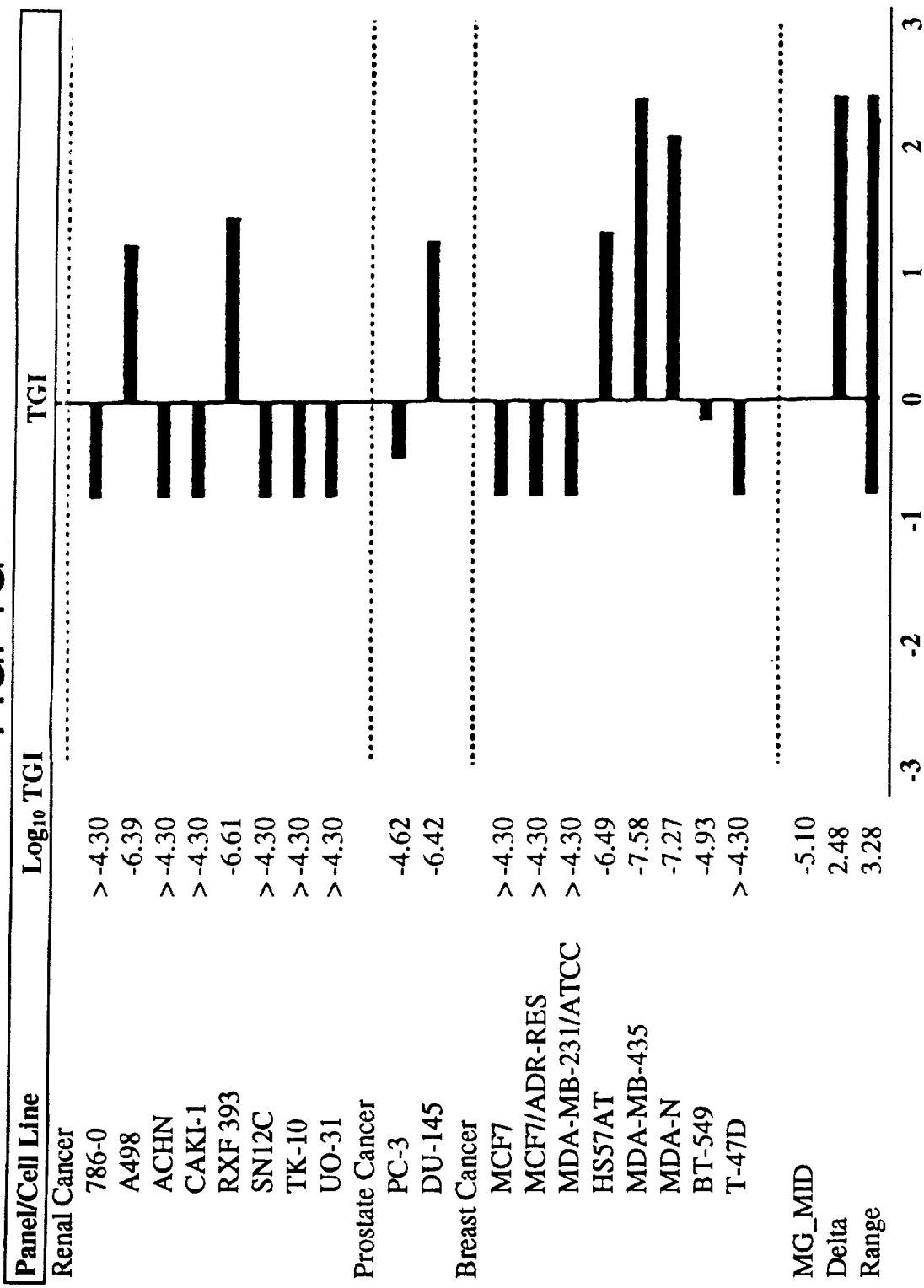
Figure 1H:
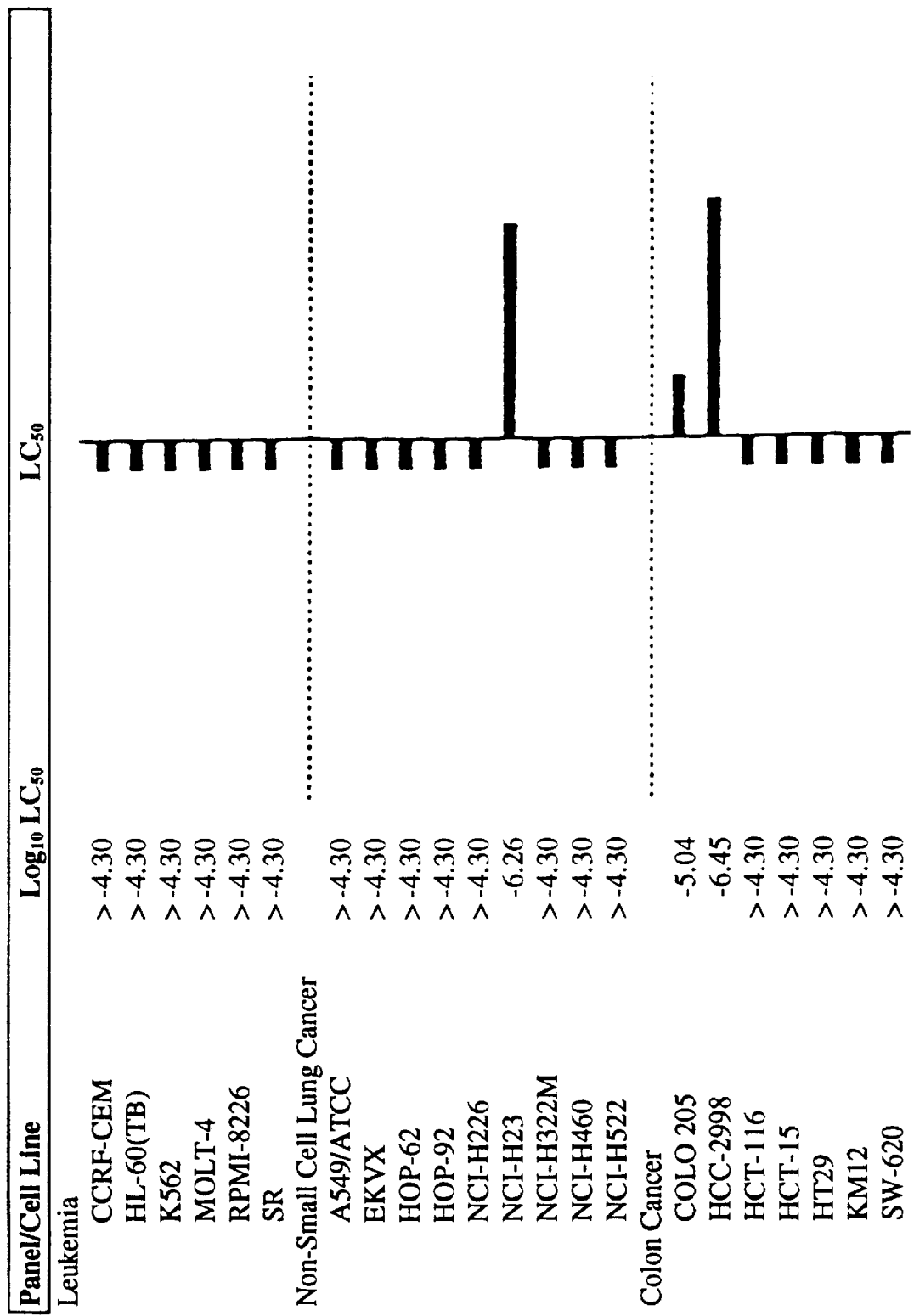
Figure 1I:
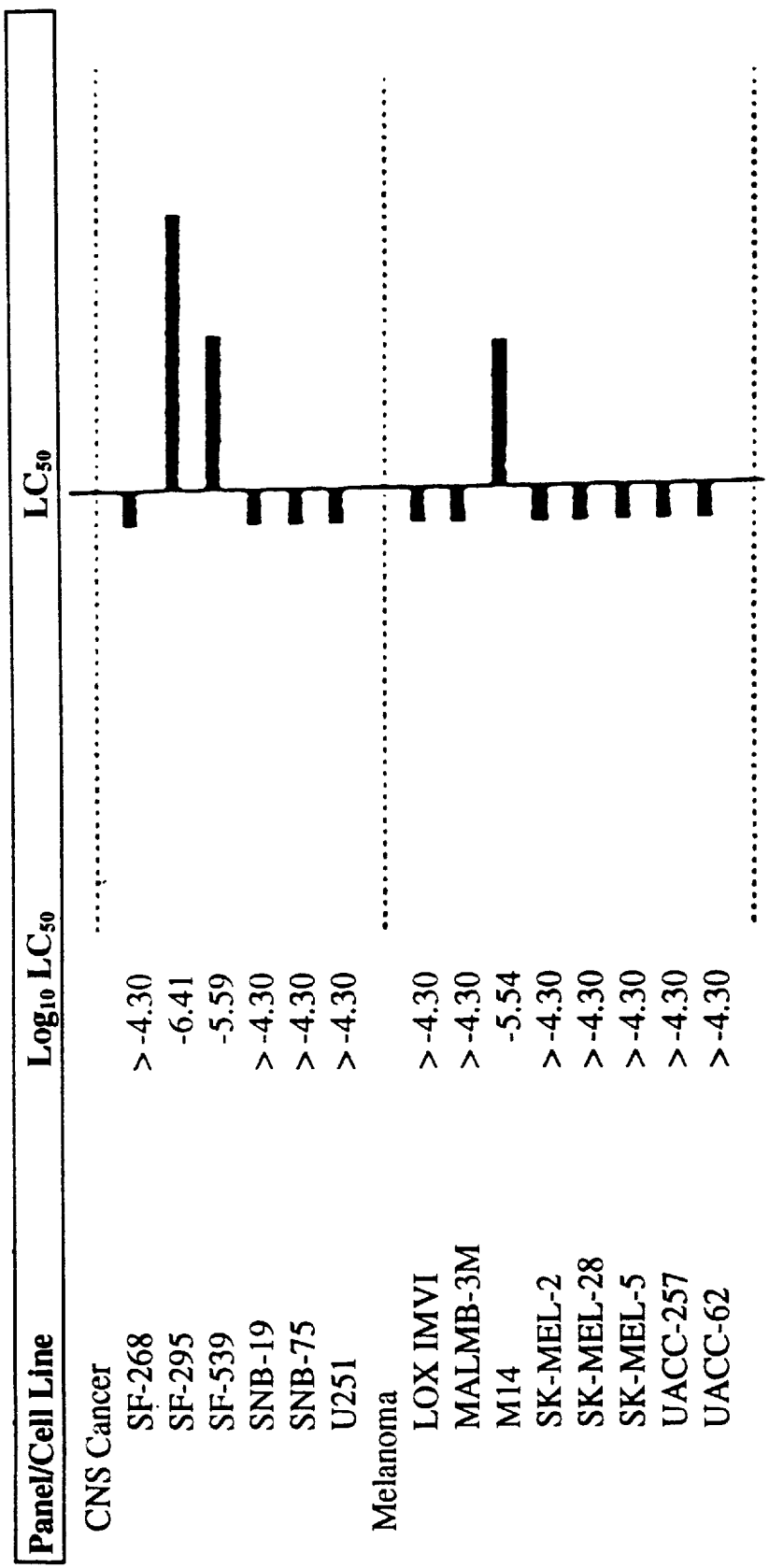
Figure 1J:
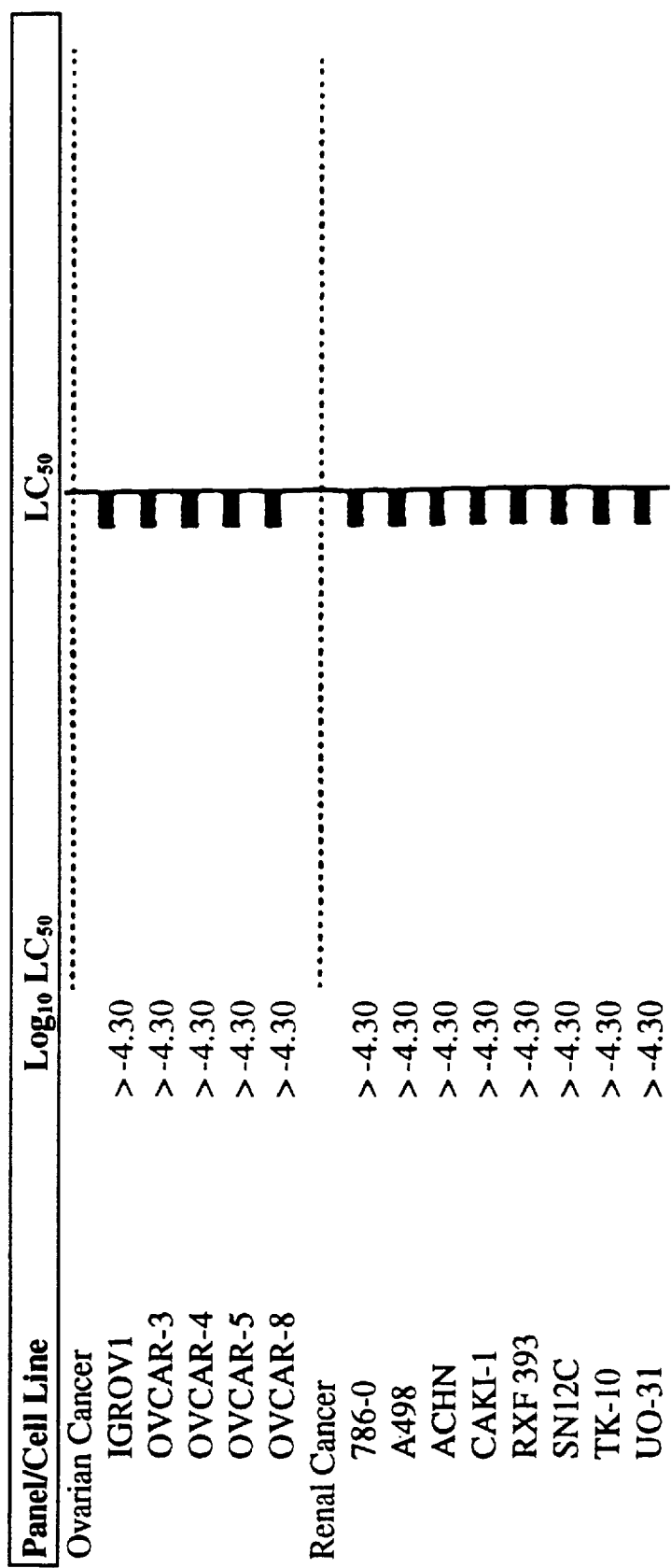
Figure 1K:
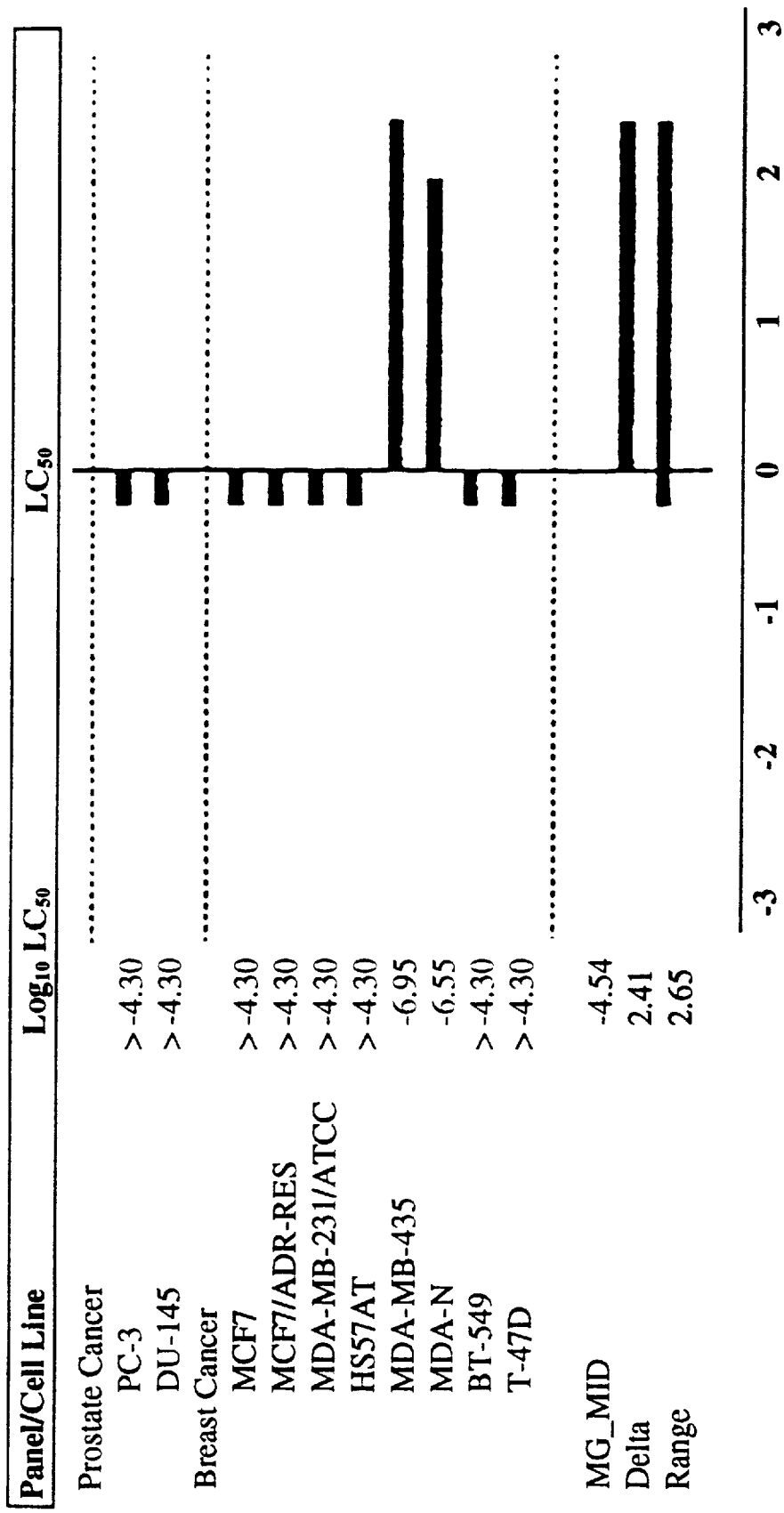

In one embodiment, the objects of the invention are accomplished by the provision of the biologically active compounds that have a structure according to the formula (I), below:

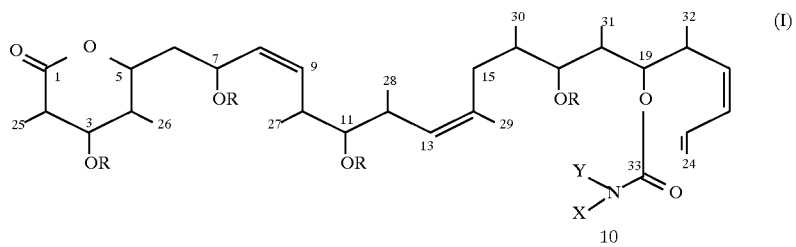
(I)

wherein:
R=—H, —A, —CH₂—Q, —COA, or —COZ,
A=lower alkyl
Z=monocyclicaryl,
Q=phenyl, tolyl, or xylyl,
X=—H, —A, —Z, or —CH₂—Z, and
Y=—H, —A, —Z, —CH₂—Z, —COA, —COZ, and acid addition salts thereof.

Various enantiomers of the discodermolides, as defined above, can be synthesized by persons of ordinary skill in the art. The natural discodermolide isolated from marine sponges is predominantly found to be the (+) enantiomer.

Preferred compounds of the invention are represented by the formula:

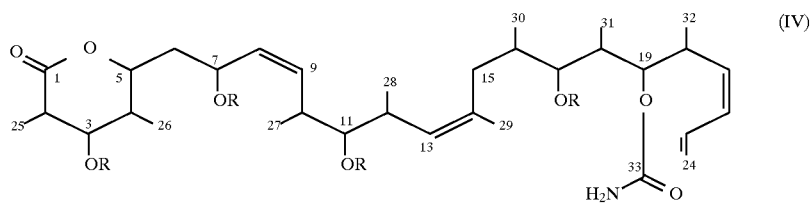
(IV)

Compounds which are variants of structure (I) have also been discovered and can include the octahydro-, tetrahydro-, and 23-24-dihydro-derivatives of compounds according to the above formulae. The compounds may be a single geometrical isomer or mixtures thereof (E or Z isomer). These variant compounds have fewer double bonds in the carbon chain backbone. It is well known that the double bonds in the carbon chain backbone of structure (I) can be selectively saturated to yield, for example, tetrahydro- or dihydro-compounds according to the subject invention. Certain of these structures are shown as formulae (II) and (III), below.

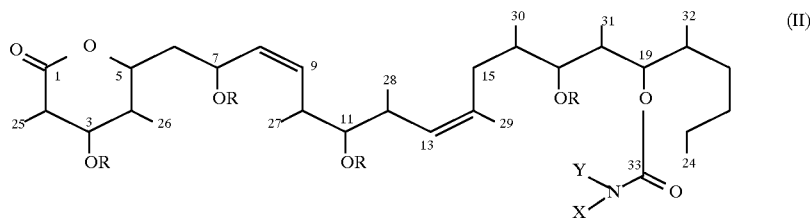
(II)

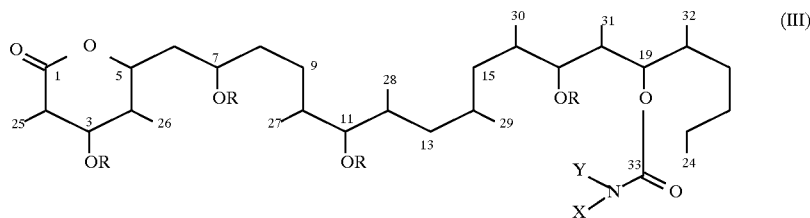
(III)

wherein:
R=—H, —A, —CH₂—Q, —COA, or —COZ,
A=lower alkyl,
Z=monocyclicaryl,
Q=phenyl, tolyl, or xylyl,
X=—H, —A, —Z, or —CH₂—Z, and
Y=—H, —A, —Z, —CH₂—Z, —COA, —COZ, and acid addition salts thereof.

wherein R=—H, or —COCH₃, or —CH₃, and by the formulae:

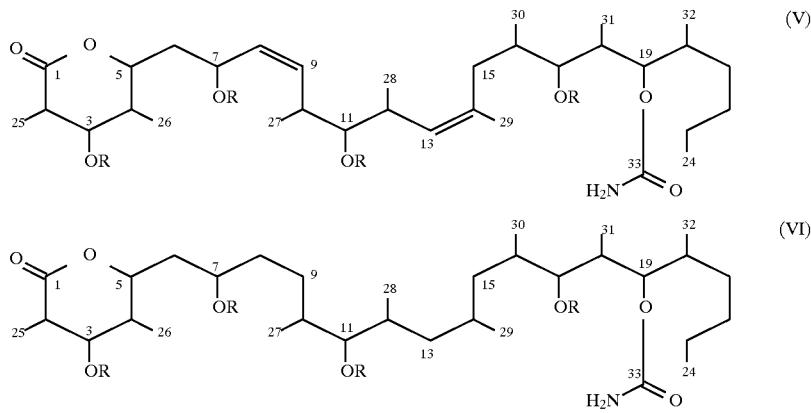

wherein R=—H, or —COCH₃, or —CH₃.

In preferred embodiments of the invention, the compounds are substantially pure, i.e., contain at least 95% of the compound as determined by established analytical methods. The most preferred embodiments of Compounds (IV), (V), and (VI) have R=H.

The lactone compounds of the subject invention and methods of preparing those compounds or compositions comprising them, are described in U.S. Pat. Nos. 4,939,168 and 5,010,099, which are hereby incorporated by reference.

Discodermolides can be isolated from the marine sponge *Discodermia dissoluta,* can be found by SCUBA off Lucay, Grand Bahama Island, at a depth of 33 meters. Thus, one method of preparation for the compounds used according to the subject invention involves extraction from marine sponges of the Genus Discodermia (Phylum Porifera, Class Demospongiae, Order Lithistida, Family Theonellidae). Collection details are listed below:

high, and joined at the base. The sponges are white or pinkish-white, and are firm but slightly compressible. Discodermia sp. IV is an irregular, stalked, shallow cup, 5–10 cm in diameter and 3–5 cm high. The sponges are cream to yellow, and the consistency is firm and not compressible. For complete descriptions of these samples, refer to Kelly-Borges, M., Robinson, E. V., Gunasekera, S. P., Gunasekera, M., Gulavita, N. K., and Pomponi, S. A. 1994. Species differentiation in the marine sponge genus Discodermia (Demospongiae:Lithistida): the utility of ethanol extract profiles as species-specific chemotaxonomic markers. *Biochemical Systematics and Ecology,* 22(4): 353–365. All samples cited herein with HBOM catalog numbers are deposited in the Harbor Branch Oceanographic Museum, Fort Pierce, Fla. All specimens are preserved in 70% ethanol with an expected shelf life of at least 30 years and are accessible to those skilled in the art for taxonomic identification purposes.

| Species | HBOM No. | Location | Latitude | Longitude | Depth | Collection Method |
|---|---|---|---|---|---|---|
| *Discodermia dissoluta* | 003:00060 | Lucaya, Grand Bahama Is., Bahamas | 26°30'N | 78°38'W | 100 ft. | scub |
| *Discodermia dissoluta* | 003:00876 | | | | | |
| *Discodermia dissoluta* | 003:00877 | Egg Island, Bahamas | 25°30'N | 76°54'W | 110 ft. | scuba |
| Discodermia sp. IA | 003:00854 | Goulding Cay, New Providence Island, Bahamas | 24°46'N | 77°24'W | 592 ft. | manned submersible |
| Discodermia sp. IA | 003:00855 | Goulding Cay, New Providence Island, Bahamas | 24°60'N | 77°33'W | 608 ft. | manned submersible |
| Discodermia sp. IA | 003.00856 | Goulding Cay, New Providence Island, Bahamas | 24°60'N | 77°33'W | 585 ft. | manned submersible |
| Discodermia sp. IA | 003:00858 | Sweetings Cay, Grand Bahama Is. Bahamas | 26°32'N | 77°53'W | 515 ft. | manned submersible |
| Discodermia sp. IV | 003:00871 | Chub Cay, Bahamas | 25°24'N | 77°55'W | 656 ft. | manned submersible |
| Discodermia sp. IV | 003:00873 | Andros Island, Bahamas | 23°52'N | 77°27'W | 556 ft. | manned submersible |

*Discodermia dissoluta* Schmidt, 1880 (*Die spongien des Meerbusen von Mexico (und des Caraibischen Meeres*], *III Abt Tetractinelliden, Monactinelliden, und Anhang. II Heft.* G. Fischer, Jena, pp. 35–90) is an amorphous to lobate sponge, 4 cm in diameter and up to 7 cm thick, dark brown externally and cream-colored internally. The consistency is firm but compressible. The other samples are new, unnamed species. Discodermia sp. IA is a cluster of tubes, up to 15 cm In preferred embodiments for production of the new compounds by extraction from marine sponges, etc., suitable organic solvent systems for extraction can be selected from methanol, ethyl acetate, toluene, heptane, hexane, isooctane, acetone, benzene, diethyl ether, t-butyl methyl ether, ethanol, isopropanol, 1,2-dichloroethane, and, especially, chloroform and dichloromethane. Mixtures of two or more of such solvents in various ratios and combinations are advantageous.

Compounds of the invention are isolated by various fractionation and chromatographic techniques from the extracts obtained as disclosed. Preferred isolation procedures include various chromatography techniques, e.g., column chromatography, medium pressure column chromatography, and countercurrent chromatography with suitable columns, including multi-layer planetary coil columns. A variety of solvents are available for use as single or mixed eluents, such as methylene chloride, methanol, ethyl acetate, acetonitrile, n-propanol, n-butanol, water, and equivalent solvents. Further purifications using such procedures may also be carried out on the recovered extractions. Preferred isolation techniques for further purification include chromatographic operations such as high-pressure liquid chromatography with suitable columns with suitable solvent, particularly, methylene chloride/methanol or methanol/water mixtures.

Modifications of the novel discodermolide compound can readily be made by those skilled in the art.

With a knowledge of the compounds of the subject invention, and their structures, skilled chemists can use known procedures to synthesize these compounds from available substrates. For example, synthetic methods for producing certain of these compounds are described in Nerenberg et al., supra.

In further preferred methods of the invention, new salts within the scope of the invention are made by adding mineral acids, e.g. HCl, $H_2SO_4$, etc., or strong organic acids, e.g., formic, oxalic, etc., in appropriate amounts to form the acid addition salt of the parent compound or its derivative. Also, synthesis type reactions may be used pursuant to known procedures to add or modify various groups in the preferred compounds to produce other compounds within the scope of the invention.

The scope of the invention is not limited by the specific examples and suggested procedures and uses related herein since modifications can be made within such scope from the information provided by this specification to those skilled in the art.

As used in this application, the terms "analogs," "variants" and "derivatives" refer to compounds which are substantially the same as another compound but which may have been modified by, for example, adding additional amino acids or side groups. The terms "analogs," "variants" and "derivatives" as used in this application also may refer to compounds which are substantially the same as another compound but which have atomic or molecular substitutions at certain locations in the compound.

As described, a preferred embodiment of the discodermolide compounds comprises the structure shown in structures (IV), (V), and (VI), wherein R is H. However, analogs or derivatives of this preferred embodiment can be readily prepared using commonly known, standard reactions. These standard reactions include, but are not limited to, hydrogenation, methylation, acetylation, and acidification reactions.

An example of one analog which can be made according to the subject invention is octahydrodiscodermolide. To make this compound, discodermolide (2.0 mg) in EtOH (4.0 ml) was treated with a catalytic amount of Pt(IV) oxide and hydrogenated under balloon pressure at room temperature for 14 h. The product was filtered and concentrated under reduced pressure in a rotavapor maintained at room temperature to give a mixture of hydrogenated products. The crude mixture was separated by HPLC ($SiO_2$, 5 micron, 250×10 mm, 3.5% $MeOH/CH_2Cl_2$) to yield pure octahydrodiscodermolide 20SG721 and its $C_{14}$ epimer 20SG724. The yield for 20SG721 was 0.1 mg, while the yield for 20SG724 was 0.7 mg.

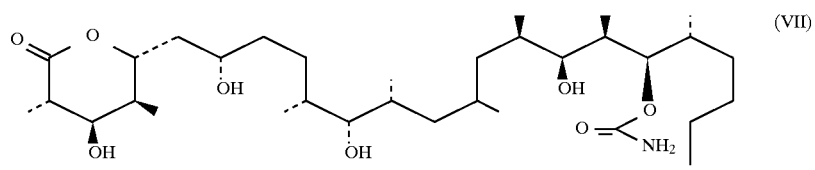

20SG721 and 20SG724 (Octahydrodiscodermolide)

Octahydrodiscodermolide (two $C_{14}$ epimers, 20SG721 and 20SG724): white solids, molecular formula $C_{33}H_{63}NO_8$.

$^1$H NMR ($CDCl_3$ and 10% $CD_3OD$)δ 4.58 (1H, dt, J=1.3, 8.8 Hz, H5), 4.54 (1H, dd, J=8.5, 2.6 Hz, H19), 3.90 (1H, m, H7), 3.63 (1H, t, J=3.5, H3), 3.21 (1H, dd, J=7.4, 3.8 Hz, H17), 3.09 (1H, dd, J=8.6, 2.7 Hz, H11), 2.64 (1H, m, H20), 1.85–1.60 (CH and $CH_2$ groups), 1.26 (3H, d, J=7.6 Hz, $CH_3$) 1.25–1.05 (CH and $CH_2$ groups), 1.01 (3H, d, J=6.8 Hz, $CH_3$), 0.92 (3H, d, J=6.6 Hz, $CH_3$), 0.83 (3H, t, J=7.3 Hz, H24), 0.83 (6H, d, J=7.2 Hz, $2\times CH_3$), 0.82 (3H, J=7.0 Hz, $CH_3$), 0.81 (3H, d, J=7.2 Hz, $CH_3$), 0.76 (3H, d, J=6.6 Hz, $HC_3$);

$^{13}$C NMR δ174.8 (s), 157.8 (s), 79.8 (d), 79.3 (d), 77.5 (d), 77.4 (d), 73.0 (d), 67.5 (d), 43.1 (d), 40.9 (t), 40.7 (t), 36.9 (d), 35.9 (d), 35.5 (d), 35.4 (d), 34.6 (t), 31.7 (d), 31.6 (d), 31.5(t), 29.6 (t), 29.1 (t), 28.5 (t), 27.3 (d), 22.8 (t), 20.6 (q), 16.0 (q), 15.7 (q), 15.6 (q), 14.0 (q), 13,1 (q), 12.6 (q), 11.4 (q), 9.1 (q).

The octahydrodiscodermolide compounds were tested for biological activity and the following results obtained:

| 20SG721 | 20SG724 |
| --- | --- |
| P388 $IC_{50}$ = 0.02 μg/ml | P388 $IC_{50}$ = 3.56 μg/ml |
| A549 $IC_{50}$ = 0.008 μg/ml | A549 $IC_{50}$ = >5 μg/ml |

As embodied and fully described herein, the invention also comprises methods of use of the new compounds and compositions of the invention, e.g., methods of inhibiting tumors in an animal, preferably a mammal. Most preferably, the invention comprises a method for the antitumor treatment of a human in need of such treatment, i.e., a human hosting cancer cells, including breast, colon, or lung tumor cells, or leukemia cells. In addition to the types of cancer cells listed above for which the subject discodermolides and compositions are particularly useful, the subject compounds have also been shown to be useful for their antiproliferative activity against certain CNS cancer cell lines, melanoma cell lines, ovarian cancer cell lines, renal cancer cell lines, and prostate cancer cell lines. It would be expected, based on the particular antiproliferative modes of action identified herein, that additional cancer cell lines would also be inhibited by these compounds.

A more complete understanding of the invention can be obtained by reference to preferred embodiments of the invention which are illustrated by the following specific examples of compounds, compositions, and methods of the invention. The following examples illustrate procedures for practicing the invention. These examples should not be construed as limiting. All percentages are by weight and all solvent mixture proportions are by volume unless otherwise noted. It will be apparent to those skilled in the art that the examples involve use of materials and reagents that are commercially available from known sources, e.g., chemical supply houses, so no details are given respecting them.

EXAMPLE 1

Effect of Discodermolide on the Constitutitve Proliferation of Lymphoid and Non-Lymphoid Cell Lines of Murine or Human Origin The effects of discodermolide on the inhibition of constitutive proliferation of a number of lymphoid and non-lymphoid cell lines of mouse or human origin was investigated. The results are summarized in Table 1.

TABLE 1

Effect of discodermolide on constitutive proliferation of murine and human cell lines

| Immune Response | $IC_{50}$, nm[a] | Toxicity, nm[a] |
|---|---|---|
| Murine: Lymphoid[b] | | |
| 70Z/3 Pre-B Proliferation | 3 | 10 |
| EL-4 Thymoma Proliferation | 30 | 100 |
| Murine: Non-Lymphoid[b] | | |
| Swiss 3TC Proliferation | 37 | ND[c] |
| BMSC 8.3 Proliferation[d] | 50 | ND |
| BMSC 8.6 Proliferation | 84 | ND |
| BMSC 25.4 Proliferation | 59 | ND |
| F7 Fibroblast Proliferation | 60 | ND |
| Human: Non-Lymphoid[b] | | |
| Normal Fibroblast Proliferation | 15 | >3000 |

[a]Best response
[b]Cyclosporin A activity: 100 nm for 70Z/3, 500 nm for EL-4, no inhibition for 3T3 and BMSC lines up to 1 μg/ml, not tested in F7, no inhibition for human fibroblasts up to 3 μM.
[c]Not determined
[d]Bone marrow stromal cells (MBSC) derived from CS7BL/6 mice.

Discodermolide inhibited the proliferation of murine lymphoid and non-lymphoid cell lines with $IC_{50}$ values ranging from 3 to 60 nm. The proliferation of. human non-lymphoid (foreskin fibroblast) cells was also inhibited by discodermolide ($IC_{50}$=15 nm) but viable cell recovery (toxicity) at concentrations of the compound up to 3.0 μM was not affected.

EXAMPLE 2

Anti-Proliferative Effects of Discodermolide on Human Tumor Cell Lines

Discodermolide was additionally evaluated for its antiproliferative effects utilizing the National Cancer Institute's in vitro tumor cell line panel. The results of these analyses are shown in the mean graphs presented as FIGS. 1A–1K. The data are presented using known and accepted measurements of "Growth Inhibition-50" ($GI_{50}$), where growth of 50% of the cells is inhibited; "Total Growth Inhibition" (TGI), where growth of all cells is inhibited, i.e., cytostasis; and "Lethal Concentration-50" ($LC_{50}$), where 50% of the cells are killed. Of the approximately 60 cell lines tested, discodermolide demonstrated selective cytotoxicity (as indicated to the bars of the right of the midline) for 32 cell lines for $GI_{50}$ and 18 cell lines for TGI. According to $LC_{50}$ measurements for the NCI cell lines, the subject compound tested was particularly effective against human non-small cell lung cancer (NCI-H23), human colon cancers (COLO 205 and HCC-2998), human melanoma (M14), two of six CNS cancer cell lines (SF 295 and SF 539), and two of eight breast cancer cell lines (MDA-MB-435 and MDA-N). A statistical analysis of this selective toxicity pattern (the COMPARE algorithm) indicated that discodermolide's cytotoxicity pattern matched that of several previously tested microtubule interactive agents, including the pattern generated by taxol.

EXAMPLE 3

Effect of Discodermolide on Cell Cycle Progression of GI-101A Human Breasts A549 Human Lung, and Jurkat Human Leukemia Cells in Comparison to Taxol Cell cycle studies were initiated in order to pinpoint a specific phase within the cell cycle in which discodermolide was exerting its antiproliferative effect. GI-101A human breast and A549 human lung cells were used as cell cycle targets to compare the effects of discodermolide and taxol on perturbation of the cell cycle. Cell cycle analyses were performed as follows: GI-101A and A549 cells were incubated at 37° C. in 10% $CO_2$ in air in the presence or absence of varying concentrations of discodermolide or taxol (purchased from Molecular Probes, Eugene, Oreg.) for 48 hours. Cells were harvested, fixed in ethanol, and stained with 0.5 mg/ml of propidium iodide (P.I.) together with 0.1 mg/ml of RNase A. This procedure permeabilizes live cells and allows entry of P.I. to stain DNA. Stained preparations were analyzed on a Coulter EPICS ELITE with 488 nm excitation with the dead cells excluded by back-gating of P.I. preparations without detergent on forward and side scatter histograms. Fluorescence measurements and resulting DNA histograms were collected from at least 5,000 P.I. stained cells at an emission wavelength of 690 nm. Raw histogram data were further analyzed using a cell cycle analysis program (Multicycle, Phoenix Flow Systems). The results of these experiments are shown in FIGS. 2A–2C and 3A–3C.

Figure 2A:
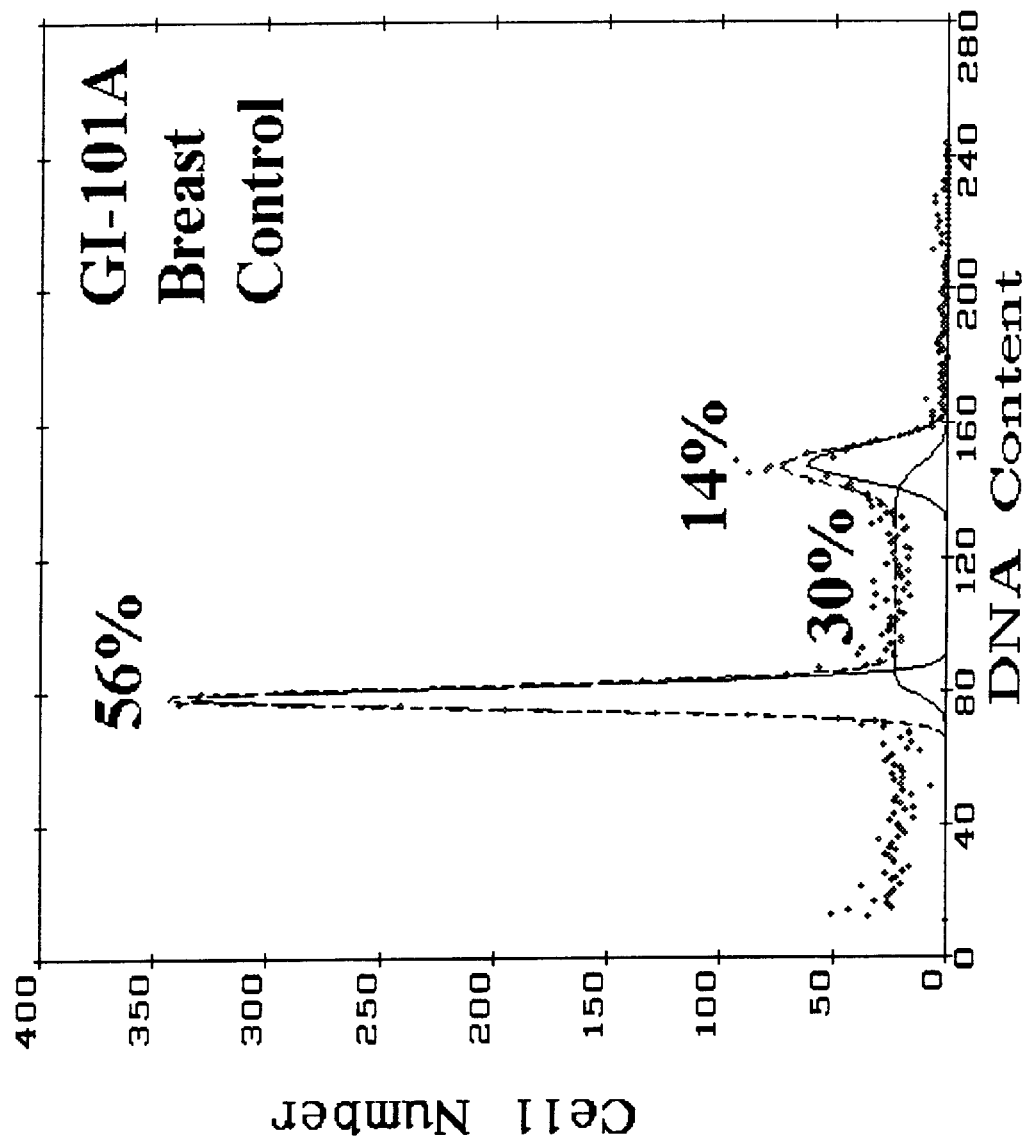
Figure 2C:
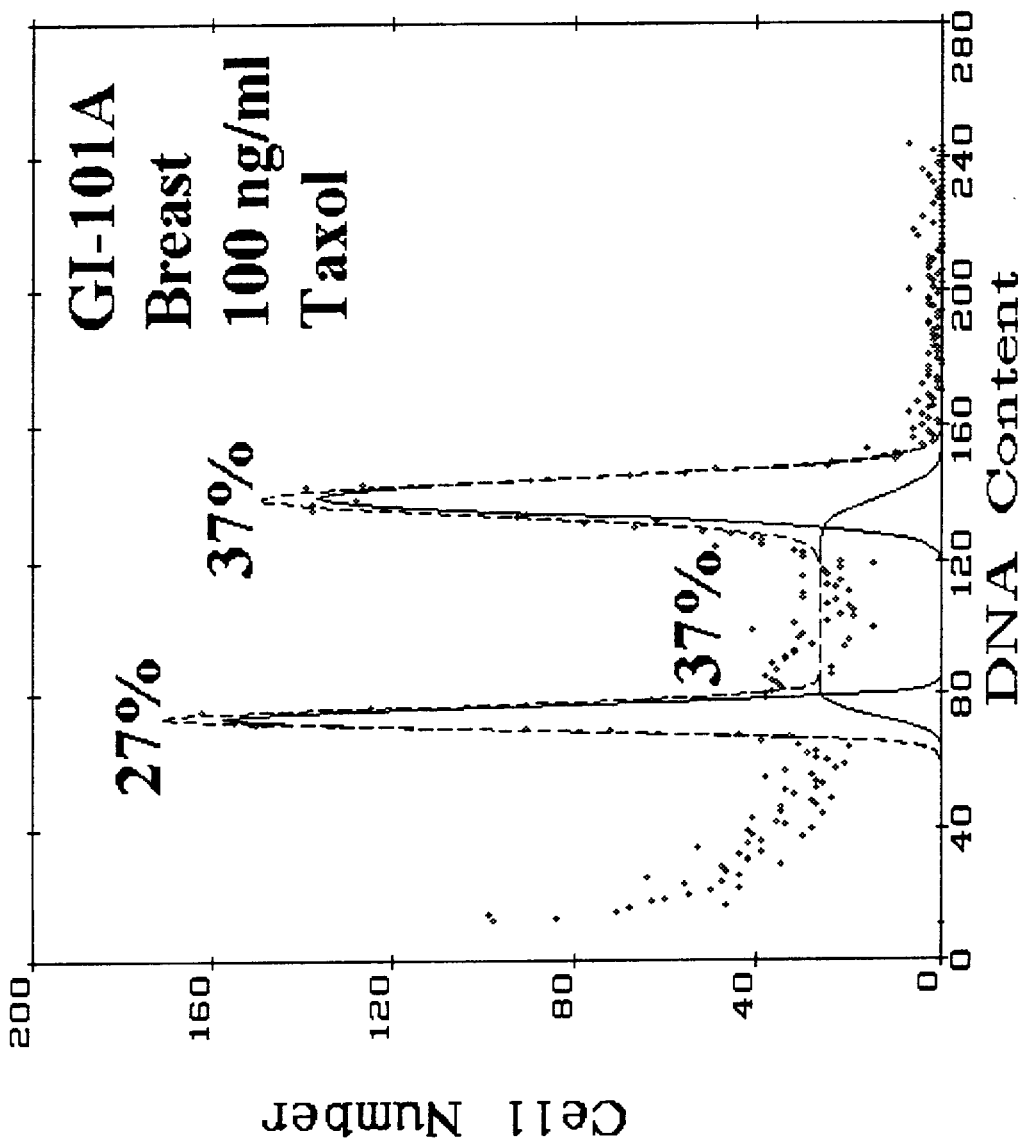

Control cultures of GI-101A breast cells demonstrated a characteristic pattern of cell cycling. Approximately 56% of the control cells comprise the $G_1$ phase of the cell cycle, and 30% comprise the S phase. Only approximately 14% of cells are demonstrable in the $G_2$/M phase in asynchronous cultures at any one time mainly due to their high proliferative rate (FIG. 2A). At 24 hours post culture initiation with 100 ng/ml of discodermolide, the percentage of cells in $G_1$ phase decreased to 22%. The percentage of S phase cells increased from 30% to 41% while the percentage of cells in $G_2$/M increased dramatically from 14% in the control to 38% in discodermolide treated cells (FIG. 2B), indicating a block at $G_2$/M phase of the cell cycle. GI-101A cells treated with taxol for 24 hours demonstrated almost identical effects. The percentage of cells in $G_1$ decreased from 56% in the control to 27% in taxol-treated cultures. The percentage of S-phase cells increased from 30% to 37%, while the percentage of $G_2$/M-phase cells increased from 14% in control to 37% in taxol-treated cultures, indicating a block at $G_2/M$ (FIG. 2C). These results indicated that both discodermolide and taxol exerted similar effects on the proliferation of GI-101A cells, namely, blockage of cell proliferation at the $G_2/M$ phase of the cell cycle.

Figure 3B:
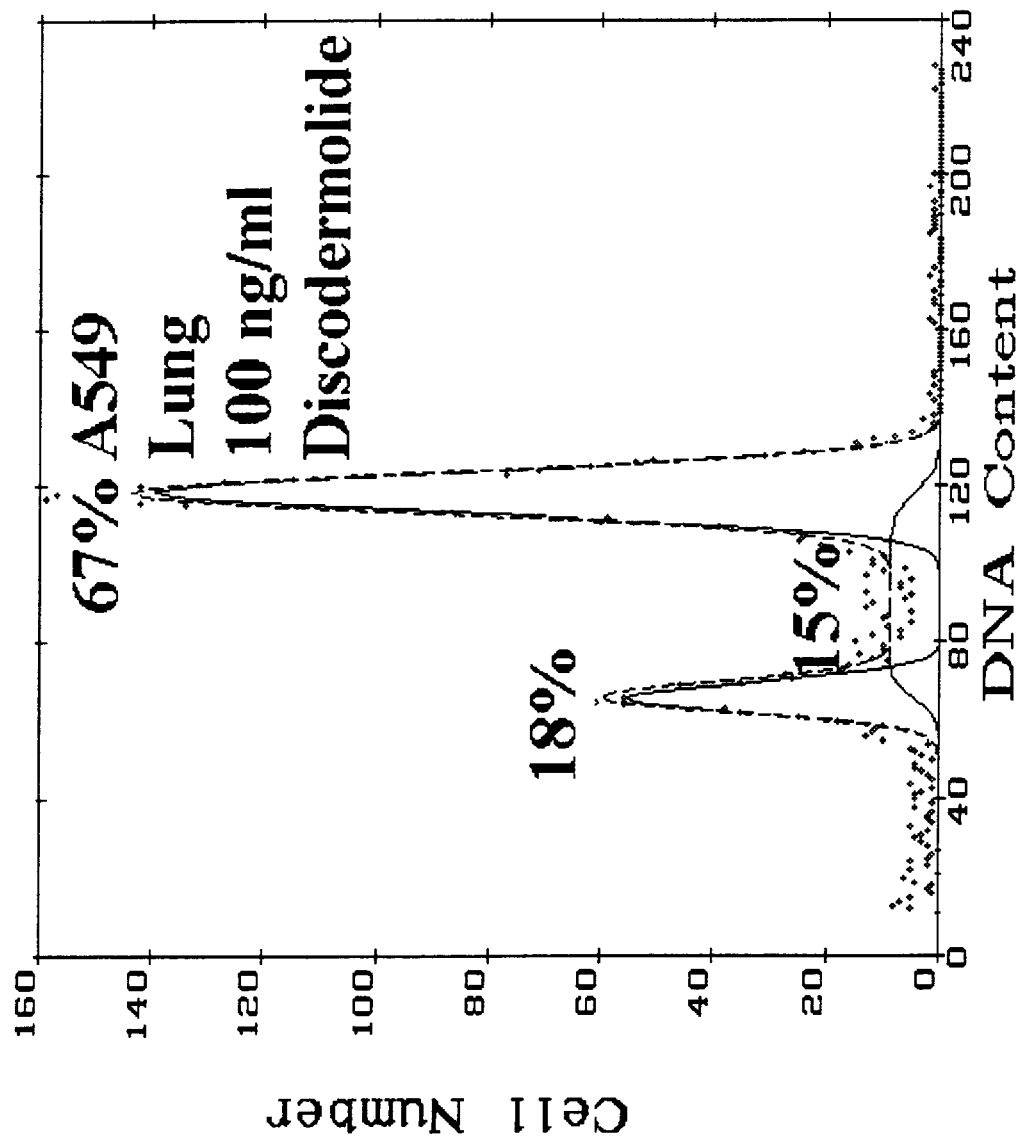
Figure 3C:
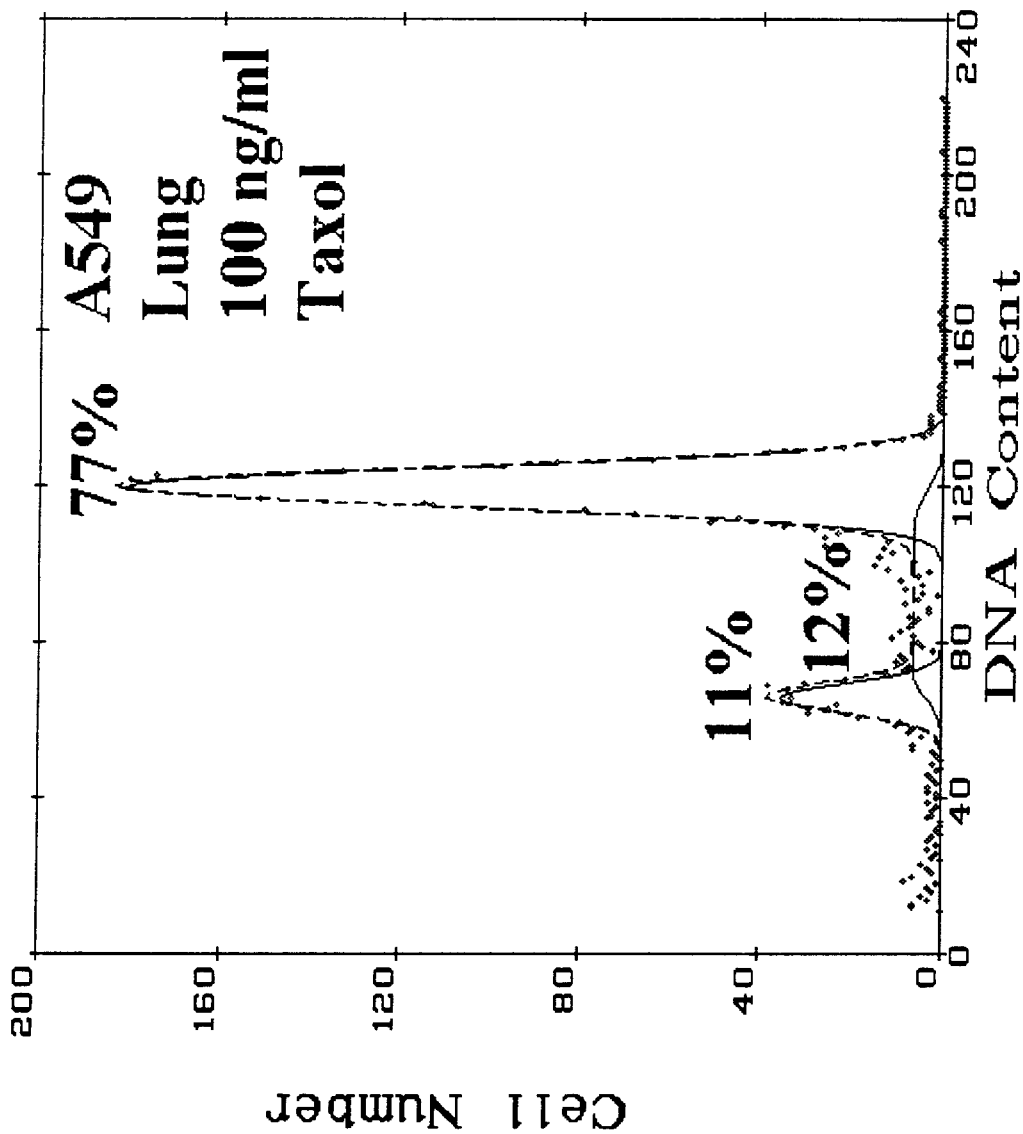

Discodermolide and taxol were compared for their effects on the proliferation of A549 human lung cells. Cell cultures were similarly initiated in the presence and absence of various concentrations of discodermolide or taxol and incubated at 37° C. in 10% $CO_2$ in air for 48 hours. Cells were harvested and stained and analyzed on the flow cytometer as outlined above. Control cultures of A549 cells exhibited normal cycling patterns for this line, with approximately 77% of the cells in $G_1$, 19% in S phase, and only 4% present in the $G_2/M$ phase of the cell cycle (FIG. 3A). Treatment of cells with 100 ng/ml of discodermolide resulted in a decrease in the percentage of cells in $G_1$ from 77% in the control to 18% in discodermolide-treated cells and a dramatic increase in the percentage of cells in $G_2/M$ from 4% in the control to 67% in discodermolide-treated cells (FIG. 3B). Taxol treatment of A549 cells resulted in almost identical results with the percentage of cells in $G_1$ decreasing from 77% in the control to 11% in taxol-treated cells and the percentage of cells in $G_2/M$ increasing from 4% in the control to 77% in taxol-treated cells (FIG. 3C). The percentage of S phase cells in both groups did not change significantly. These results indicate that discodermolide and taxol have similar $G_2/M$ blocking effects on A549 human lung cells.

Figure 4C:
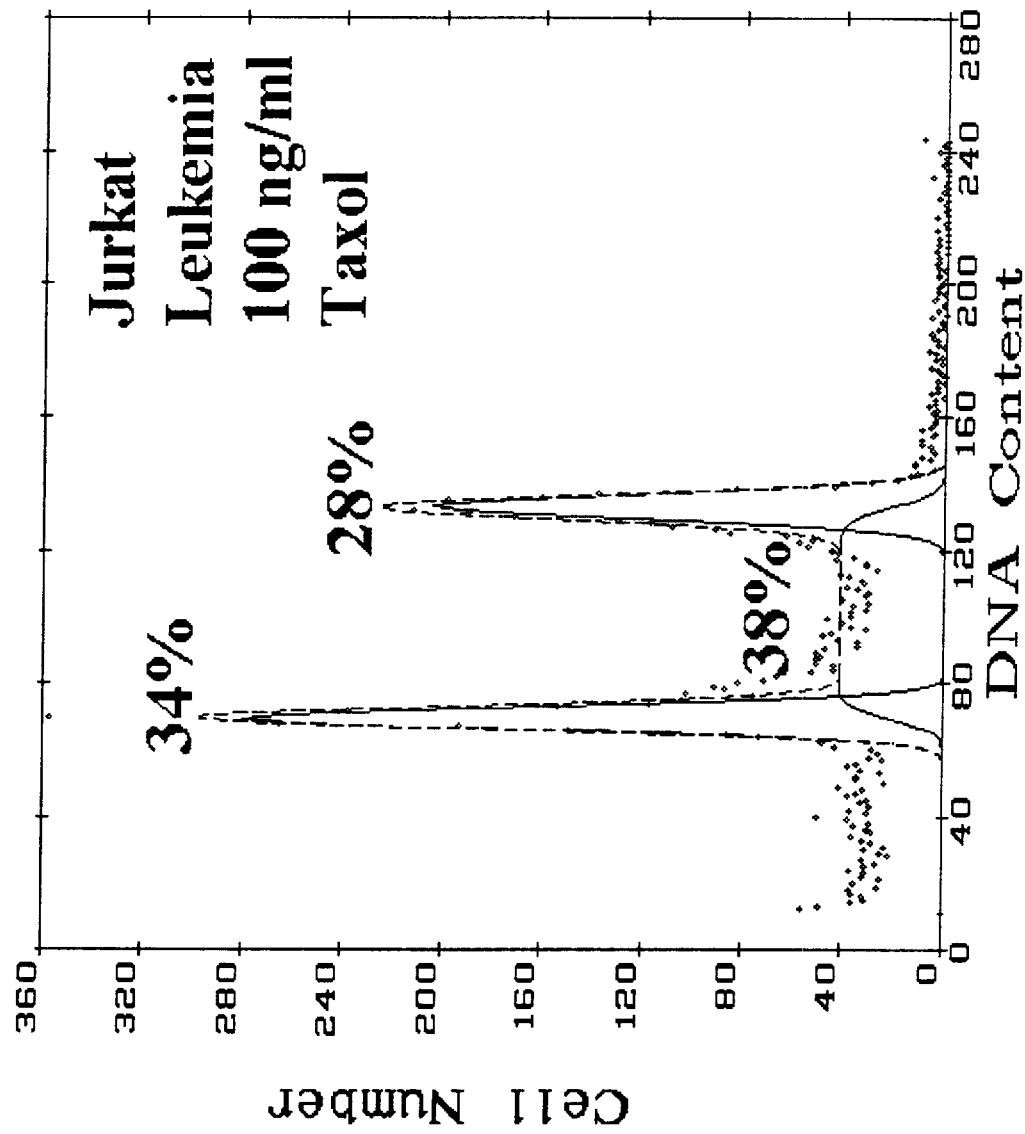

Discodermolide and taxol were compared for their effects on the proliferation of Jurkat human leukemia cells. Cell cultures were similarly initiated in the presence and absence of various concentrations of discodermolide or taxol and incubated at 37° C. in 10% $CO_2$ in air for 48 hours. Cells were harvested and stained and analyzed on a flow cytometer using standard procedures. Control cultures of Jurkat cells exhibited normal cycling patters for this line, with approximately 68% of the cells in $G_1$, 25% in S-phase, and 7% present in the $G_2/M$-phase of the cell cycle (FIG. 4A). Treatment of cells with 100 ng/ml of discodermolide resulted in a decrease in the percentage of cells in $G_1$ from 68% in the control to 35% in discodermolide-treated cells and a dramatic increase in the percentage of cells in $G_2/M$ from 7% in the control to 27% in discodermolide-treated cells (FIG. 4B). Taxol treatment of Jurkat cells resulted in almost identical results with the percentage of cells in $G_1$ decreasing from 68% in the control to 34% in taxol-treated cells and the percentage of cells in $G_2/M$ increasing from 7% in the control to 28% in taxol-treated cells (FIG. 4C). The percentage of S-phase cells in both groups increased from 25% in the control to 38% in both discodermolide- and taxol-treated cells. These results indicate that discodermolide and taxol have similar $G_2/M$-blocking effects on Jurkat human leukemia cells.

EXAMPLE 4

Effect of Discodermolide on Human Breast Carcinoma Cells

The effect of discodermolide on two human breast carcinoma cell lines, estrogen receptor positive MCF-7 cells, and estrogen receptor negative MDA-MB-231 cells, was determined. The results were compared with those obtained by treatment with taxol. Both lines were examined for drug effects on growth and by indirect immunofluorescence for effects on the microtubule cytoskeleton. The results were similar for both lines. The $IC_{50}$ for discodermolide was 2.4 nm, similar to the 2.1 nm value obtained with taxol. Immunofluorescence patterns of discodermolide-treated cells revealed remarkable rearrangement of cellular microtubules, indicating promotion of microtubule assembly and a taxol-like effect. These patterns appeared at concentrations as low as 10 nm. Similar but less marked changes occurred with taxol treatment, but only at much higher drug concentrations (1 $\mu$m).

EXAMPLE 5

Effects of Discodermolide on Tubulin Polymerization and Stabilization

Figure 5:
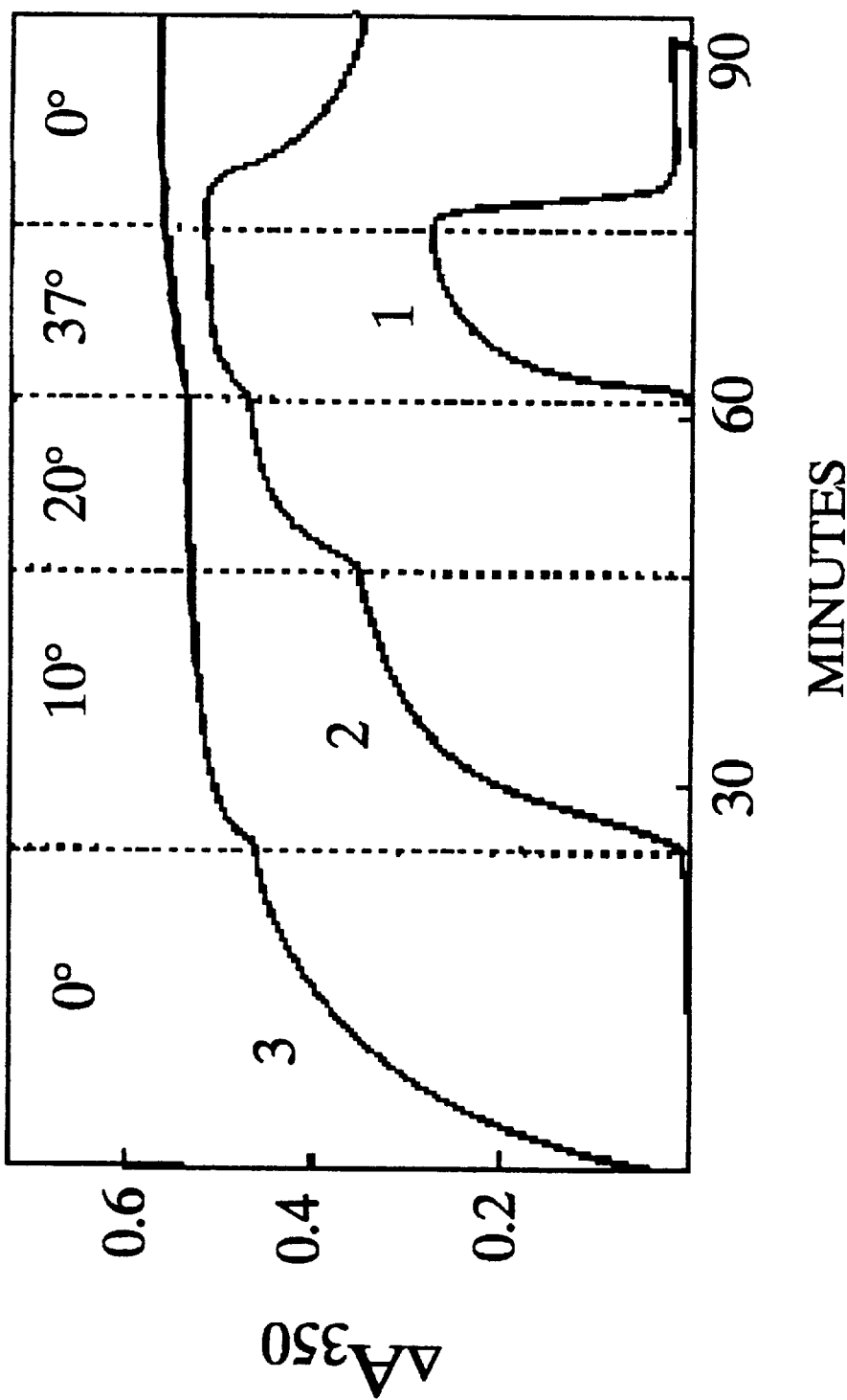
FIG. 5 shows the effect of discodermolides (compared to taxol) on tubulin polymerization according to the subject invention.

Discodermolide was analyzed for its interactions with tubulin. Tubulin polymerization was monitored turbidimetrically at 350 nm with an electronic temperature controller. Reaction mixtures contained 0.1M 4-morpholine-ethanesulfonate (pH 6.9), 1.0 mg/ml (10 $\mu$M) electrophoretically-homogenous bovine brain tubulin freed of unbound nucleotide by gel filtration, 0.5 mg/ml heat-treated MAPs, 100 $\mu$M GTP, and 4% (v/v) dimethylsulfoxide. A concentration of 10 $\mu$M of discodermolide (curve 3) was compared with the same concentration of taxol (curve 2) and no drug (curve 1), as shown in FIG. 5. These results demonstrate that rapid polymerization began as soon as discodermolide was added to the tubulin-containing reaction mixture at 0° C. with the reaction almost complete. The taxol-containing mixture did not begin to assemble until the temperature reached 10° C., while the control (no drug) began to assemble at 37° C. Upon return of the mixture to 0° C., the control mixture disassembled as expected and there was a modest decline in the assembly of the taxol mixture, but the discodermolide mixture remained stable. We also observed in other studies that discodermolide induced the assembly of tubulin without MAPs or GTP, and these reactions were more dramatic compared to those observed with taxol, especially at low temperatures. We found in additional studies that the $EC_{50}$ value for the polymerization of tubulin by discodermolide was 2.7 $\mu$M compared to 23 $\mu$M for taxol.

Electron micrographs of polymers of tubulin formed in the presence of discodermolide, taxol, and control showed very similar characteristics, presence of polymers, microtubules, and sheets; however, the taxol-induced polymers were somewhat longer than those induced with discodermolide, and control polymers were even longer than either discodermolide or taxol-induced preparations.

The results from this study suggest that the mechanism of action of discodermolide is superior to that of taxol in regard to stabilization of microtubules.

EXAMPLE 6

Formulation and Administration

The compounds of the invention are useful for various non-therapeutic and therapeutic purposes. It is apparent from the testing that the compounds of the invention are effective for inhibiting cell growth. Because of the antiproliferative properties of the compounds, they are useful to prevent unwanted cell growth in a wide variety of settings including in vitro uses. They are also useful as standards and for teaching demonstrations. They can also be used as ultraviolet screeners in the plastics industry since they effectively absorb UV rays. As disclosed herein, they are also useful prophylactically and therapeutically for treating cancer cells in animals and humans.

Therapeutic application of the new compounds and compositions containing them can be contemplated to be accomplished by any suitable therapeutic method and technique presently or prospectively known to those skilled in the art. Further, the compounds of the invention have use as starting materials or intermediates for the preparation of other useful compounds and compositions.

The dosage administration to a host in the above indications will be dependent upon the identity of the cancer cells, the type of host involved, its age, weight, health, kind of concurrent treatment, if any, frequency of treatment, and therapeutic ratio.

The compounds of the subject invention can be formulated according to known methods for preparing pharmaceutically useful compositions. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of the bioactive compound(s) is combined with a suitable carrier in order to facilitate effective administration of the composition.

In accordance with the invention, pharmaceutical compositions comprising, as an active ingredient, an effective amount of one or more of the new compounds and one or more non-toxic, pharmaceutically acceptable carrier or diluent. Examples of such carriers for use in the invention include ethanol, dimethyl sulfoxide, glycerol, silica, alumina, starch, and equivalent carriers and diluents.

To provide for the administration of such dosages for the desired therapeutic treatment, new pharmaceutical compositions of the invention will advantageously comprise between about 0.1% and 45%, and especially, 1 and 15%, by weight of the total of one or more of the new compounds based on the weight of the total composition including carrier or diluent. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A compound having the formula:

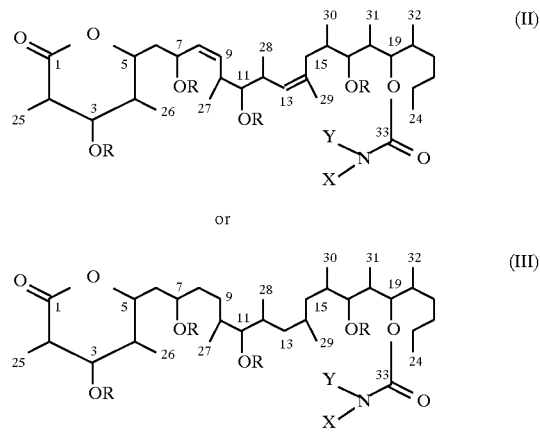

wherein:

R=—H, —A, —CH$_2$—Q, —COA, or —COZ,

A=lower alkyl,

Z=monocyclicaryl,

Q=phenyl, tolyl, or xylyl,

X=—H, —A, —Z, or —CH$_2$—Z, and

Y=—H, —A, —Z, —CH$_2$—Z, —COA, —COZ, and acid addition salts thereof.

2. The compound, according to claim 1, wherein said compound has the formula:

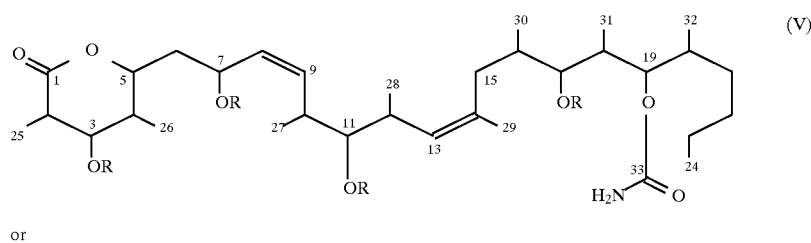

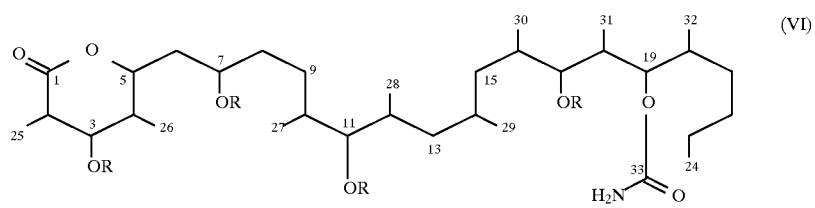

wherein R=—H, —COCH$_3$, or —CH$_3$.

3. The compound, according to claim 2, wherein R=—H.

4. A pharmaceutical composition for treating a patient hosting cancer cells, said composition comprising a discodermolide compound having the formula:

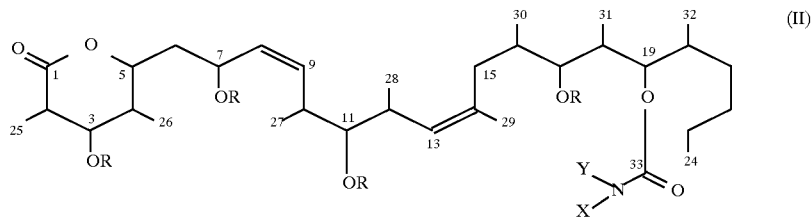

(II)

or

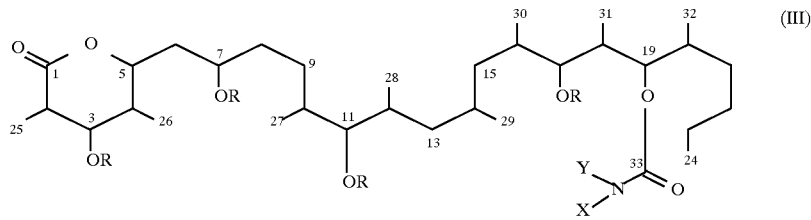

(III)

wherein:
R=—H, —A, —CH$_2$—Q, —COA, or —COZ,
A=lower alkyl,
Z=monocyclicaryl,
Q=phenyl, tolyl, or xylyl,
X=—H, —A, —Z, or —CH$_2$—Z, and
Y=—H, —A, —Z, —CH$_2$—Z, —COA, —COZ, and acid addition salts thereof, and a pharmaceutically acceptable carrier.

5. The pharmaceutical composition, according to claim 4, wherein said discodermolide compound has the formula:

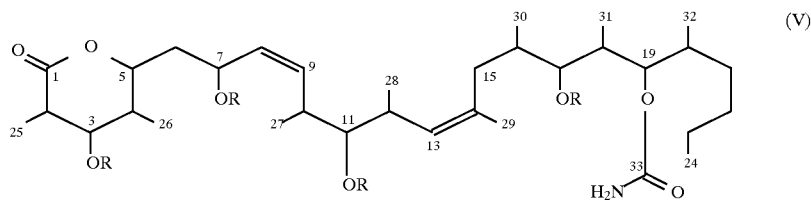

(V)

or

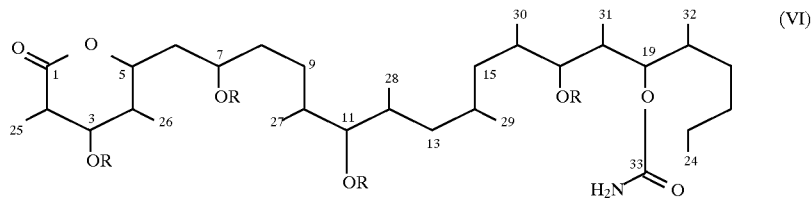

(VI)

wherein R=—H, —COCH$_3$, or —CH$_3$.

6. The pharmaceutical composition, according to claim 4, wherein said discodermolide compound has the formula:

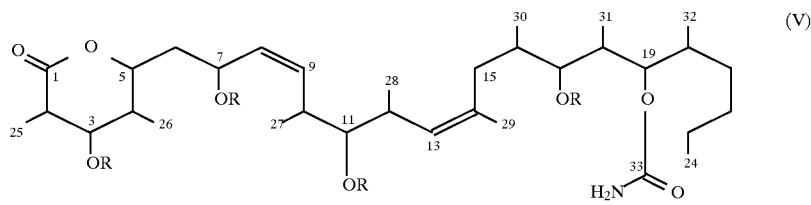
(V)
or
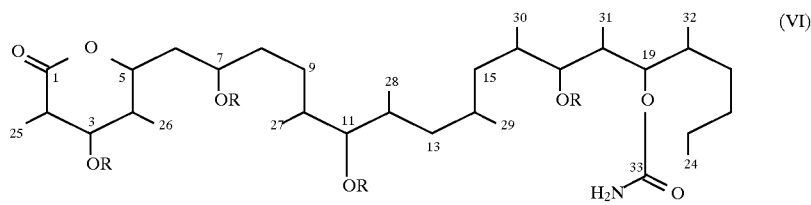
(VI)
wherein R=—H.
7. A pharmaceutical composition comprising a compound having the formula:
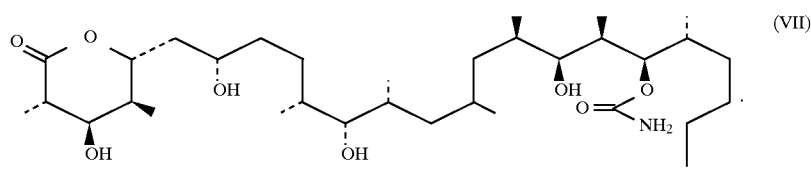
(VII)
* * * * *

UNITED STATES PATENT AND TRADEMARK OFFICE
CERTIFICATE OF CORRECTION

PATENT NO. : 5,840,750
DATED : November 24, 1998
INVENTOR(S) : Ross E. Longley, Sarath P. Gunasekera, Shirley A. Pomponi It is certified that error appears in the above-identified patent and that said Letters Patent is hereby corrected as shown below:

Column 1, line 6:"filed Dec. 5, 1995." should read --filed Dec. 5, 1995, now U.S. Patent No. 5,681,847.--.

Column 5, first line in Table "scub" should read --scuba--.

Column 9, line 53: "proliferation of. human" should read --proliferation of human--.

Column 10, line 23: "Human Breasts A549" should read --Human Breast, A549--.

Signed and Sealed this

Seventeenth Day of August, 1999

Attest:

Q. TODD DICKINSON

Attesting Officer

Acting Commissioner of Patents and Trademarks